(12) United States Patent
Kell et al.

(10) Patent No.: US 12,359,176 B2
(45) Date of Patent: Jul. 15, 2025

(54) ENGINEERED CELLS FOR PRODUCTION OF INDOLE-DERIVATIVES

(71) Applicant: Danmarks Tekniske Universitet, Kongens Lyngby (DK)

(72) Inventors: Douglas Bruce Kell, Wrexham (GB); Lei Yang, Birkerød (DK); Sailesh Malla, Nivå (DK)

(73) Assignee: Danmarks Tekniske Universitet, Kongens Lyngby (DK)

( * ) Notice: Subject to any disclaimer, the term of this patent is extended or adjusted under 35 U.S.C. 154(b) by 845 days.

(21) Appl. No.: 17/437,908

(22) PCT Filed: Mar. 13, 2020

(86) PCT No.: PCT/EP2020/056828
§ 371 (c)(1),
(2) Date: Sep. 10, 2021

(87) PCT Pub. No.: WO2020/187739
PCT Pub. Date: Sep. 24, 2020

(65) Prior Publication Data
US 2022/0145340 A1    May 12, 2022

(30) Foreign Application Priority Data
Mar. 15, 2019 (EP) .................... 19163184

(51) Int. Cl.
*C12N 9/88* (2006.01)
*C12N 9/02* (2006.01)
*C12N 9/10* (2006.01)
*C12N 15/70* (2006.01)
*C12N 15/74* (2006.01)
*C12P 17/10* (2006.01)

(52) U.S. Cl.
CPC ......... *C12N 9/1007* (2013.01); *C12N 9/0071* (2013.01); *C12N 9/1029* (2013.01); *C12N 9/88* (2013.01); *C12N 15/70* (2013.01); *C12N 15/74* (2013.01); *C12P 17/10* (2013.01)

(58) Field of Classification Search
CPC ...... C12N 9/0071; C12N 9/88; C12N 9/1029; C12N 9/1007; C12P 17/10
See application file for complete search history.

(56) References Cited

U.S. PATENT DOCUMENTS
2014/0134689 A1    5/2014 Lee et al.

FOREIGN PATENT DOCUMENTS

| EP | 2267145 | 6/2010 |
|---|---|---|
| WO | WO2006113897 | 10/2006 |
| WO | WO13093737 | 6/2013 |
| WO | WO2013127914 | 9/2013 |
| WO | WO2013127915 | 9/2013 |
| WO | WO2014134689 | 9/2014 |

(Continued)

OTHER PUBLICATIONS

P37660. UniProtKB/Swiss-Prot Database. Aug. 30, 2017.*
(Continued)

*Primary Examiner* — Yong D Pak
(74) *Attorney, Agent, or Firm* — McHale & Slavin, P.A.

(57) ABSTRACT

Integral membrane proteins capable of transporting melatonin and other indole-derivatives across biological membranes, and uses thereof.

Figure 1:
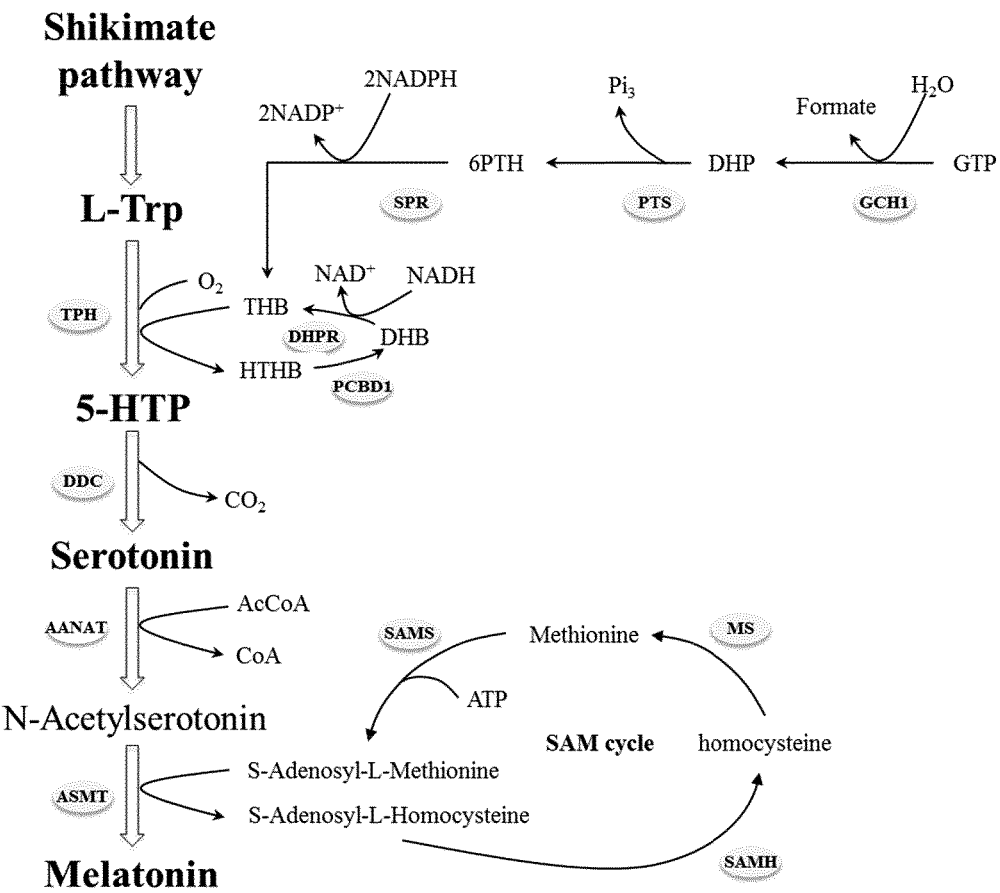

16 Claims, 12 Drawing Sheets
Specification includes a Sequence Listing.

(56) References Cited

FOREIGN PATENT DOCUMENTS

| WO | WO2015032911 | 3/2015 |
|---|---|---|
| WO | WO2017167866 | 10/2017 |
| WO | WO2017202897 | 11/2017 |
| WO | WO2018037098 | 3/2018 |
| WO | WO2018108966 | 6/2018 |

OTHER PUBLICATIONS

Byeon. Melatonin production in *Escherichia coli* by dual expression of serotonin N-acetyltransferase and caffeic acid O-methyltransferase. Appl Microbiol Biotechnol. Aug. 2016; 100(15):6683-6691. Epub Mar. 23, 2016.*
Fransceus. J Ind Microbiol Biotechnol. May 2017;44(4-5):687-695.*
Sanavia. Computational and Structural Biotechnology Journal, vol. 18, 2020, pp. 1968-1979.*
Yang. Identification and Engineering of Transporters for Efficient Melatonin Production in *Escherichia coli*. Front Microbiol. Jun. 20, 2022.*
A0A0EOXXD9_ECO1C. UniProtKB/TrEMBL Database. Feb. 28, 2018.*
A0A024L9VO_ECOLX. UniProtKB/TrEMBL Database. Feb. 13, 2019.*
A0A140ND70_ECOBD. UniProtKB/TrEMBL Database. Nov. 7, 2018.*
A0A0EOY4E3_ECO1C. UniProtKB/TrEMBL Database. Nov. 7, 2018.*
A0A077ZQA7_TRITR. UniProtKB/TrEMBL Database. Dec. 5, 2018.*
Mora-Villalobos, J. et al., "Synthetic pathways and processes for effective production of 5-hydroxytryptophan and serotonin from glucose *Escherichia coli*", Journal of Biological Engineering, vol. 12(3), pp. 1-12, XP055594649, (Mar. 2018).
Yang, W. et al, "Overexpresssion of TaCOMT improves Melatonin production and enhances drought tolerance in transgenic *Arabidopsis*", International Journal of Molecular Sciences, vol. 20(3), pp. 1-16, XP055594657, (Feb. 2019).
Huccetogullari, D. et al, "Metabolic engineering of microorganisms for production of aromatic compounds", Microbial Cell Factories, vol. 18(41), pp. 1-29, XP055594648, Feb. 2019).
Verduyn, C. et al, "Effect of benzoic acid on metabolic fluxes in yeasts: a continuous-culture study on the regulation of respiration and alcoholic fermentation", Yeast, vol. 8(7), pp. 501-517, (Jul. 1992).
Kell, D., "Control of metabolite efflux in microbial cell factories: current advances and future prospects", Internet article: http://www.osf.io/718gm/online, retrieved Oct. 2018.
Sargentini, N. et al, "Screen for genes involved in radiation survival of *Escherichia coli* and construction of a reference data base", Mutation Research, pp. 793-794, vol. 1-4, DOI: 10.1016/j.mrfmmm.2016.10.001, (2016).
Harumi, T. et al, "Simultaneous determination of serotonin, N-acetylserotonin and melatonin in the pineal gland of the juvenile golden hampster by high-performance liquid chromatography with electrochemical detection", J. Chromatogr B Biomed Appl., vol. 12(675), pp. 152-156, (Jan. 1996).
Caligiuri, M. et al, "Subunit communication in the anthranilate synthase complex from salmonella typhimurium", Science, vol. 252(5014), pp. 1845-1848, DOI: 10.1126/science.2063197, (Jun. 1991).
Lee, S. et al, "Overexpression of ethionine resistance gene for maximized production of S-adenosylmethionine in *Saccharomyces cerevisiae* sake kyokai No. 6", Korean J. Chem. Eng., vol. 27(2), pp. 587-589, (2010).
Caligiuri, M. et al, "Identificcation of amino acid residues involved in feedback regulation of anthranilate saynthase complex from salmonella typhimurium", The J. of Bio. Chem., vol. 266(13), pp. 8328-8335, (1991).
Smith, T. et al, "Comparison of biosequences", Advances in Applied Mathematics, vol. 2, pp. 482-489, (1981).
Pearson, W. et al, "Improved tools for biological sequence comparison", Proc. Natl. Acaad. Sci. USA, vol. 85, pp. 2444-2448, (Apr. 1988).
Thompson, J. et al, "CLUSTAL W: improving the sensitivity of progressive sequence alignment through sequence weighting, position-specific gap penalties and weight matrix choice", Nucleic Acids Research, vol. 22(22), pp. 4673-4680, (1994).
Needleman, S. et al, "A general method applicable to the search for similarities in the amino acid sequence of two proteins", J. Mol. Biol., vol. 48, pp. 443-453, (1970).
Park, S. et al, "Production of serotonin by dual expression of tryptophan decarboxylase and tryptamine 5-hydroxylase in *Escherichia coli*", Applied Microbiol. and Biotech., vol. 89, pp. 1387-1394, (Nov. 2010).
Rice, P. et al., EMBOSS: The European Molecular Biology Open Software Suite, European Bioinformatics Institute, UK, (2009).
Altschul, S. et al, "Basic local alignment search tool", J. Mol. Biol., vol. 215, pp. 403-410, (1990).
Young, F. et al, "Physiological and genetic factors affecting transformation of bacillus subtilis", Department of Microbiology, School of Medicine, Western Reserve University, pp. 823-829,m (Nov. 1960).
Chang, S. et al, "High frequency transformation of bacillus subtilis protoplasts by plasmid DNA", Molecular and General Genetics MGG, vol. 168, pp. 111-115, (Jan. 1979).
Koehler, T. et al, "Bacillus subtilis (natto) plasmid pLS20 mediates interspecies plasmid transfer", Journal of Bacteriology, vol. 169(11), pp. 5271-5278, (Nov. 1987).
Messing, J. et al, "A system for shotgun DNA sequencing", Nucleic Acids Research, vol. 9(2), pp. 309-321, (Oct. 1980).
Bostian, K. et al, "In vitro synthesis of repressible yeast acid phosphatase: identification of multiple mRNAs and products", Proc. Natl. Acad. Sci. USA, vol. 77(8), pp. 4504-4508, (Aug. 1980).
Bitter, G. et al, "Secretion of foreign proteins from *Saccharomyces cerevisiae* directed by a-factor gene fusions", Proc. Natl. Acad. Sci. USA, vol. 81, pp. 5330-5334, (Sep. 1984).
Database REfSeq NCBI, "Transporter *Escherichia coli*", Database accession No. WP_033554172, XP002798836, (Apr. 2020).
UniprotKB—P37660 (YHJV_ECOLI).

* cited by examiner

A

B

ENGINEERED CELLS FOR PRODUCTION OF INDOLE-DERIVATIVES

CROSS REFERENCE TO RELATED APPLICATIONS

This is a national stage filing in accordance with 35 U.S.C. § 371 of PCT/EP2020/056828, filed Mar. 13, 2020, which claims the benefit of the priority of European Patent Application No. 19163184.5, filed Mar. 15, 2019, the contents of each are incorporated herein by reference.

FIELD OF THE INVENTION

The present invention relates to integral membrane proteins capable of transporting melatonin and other indole-derivatives across biological membranes, and well as the use of such integral membrane proteins in cell factories for production of melatonin and other indole-derivatives.

BACKGROUND OF THE INVENTION

Melatonin is an antioxidant hormone produced in mammals that can be used for treating sleep disorders. One of the intermediates in the biological pathway for production of melatonin; 5-hydroxy-L-tryptophan (5HTP), has also been used as a sleep aid as well as an antidepressant. Commercial production of melatonin and 5HTP has so far predominantly relied on chemical synthesis, or, in the case of 5HTP, extraction from plants. Producing 'natural' melatonin or 5HTP biologically in so-called cell factories, i.e., cells engineered to produce these compounds, would be highly desirable. Such recombinant production of melatonin, 5HTP and other indole-derivatives from tryptophan is described in, e.g., WO 2013/127915 A1, WO 2015/032911 A1, WO 2017/167866 A1, WO 2017/202897 A1 and WO 2018/037098 A1 (Danmarks Tekniske Universitet).

Transporters are responsible for cellular exchange of both small molecules and macromolecules (Kell, 2018; WO13093737 A1 (BASF)). Transporters can be engineered to decrease intracellular product concentration, improve substrate uptake, reduce feedback inhibition or improve cellular growth. Transporters can therefore play an important role in bio-based production for improving product titers in fermentation as well as facilitating downstream purification process.

EP2267145 A1 (Evonik Degussa GmbH) relates to a process for the production of L-amino acids, in particular L-threonine, in recombinant microorganisms of the family Enterobacteriaceae, in which at the open reading frame (ORF) of yhaO is deleted, optionally together with a deletion or downregulation of, e.g., yhjV. UniProtKB database entry P37660 (YHJV_ECOLI) describes E. coli protein YhjV as an inner membrane transport protein, based on phylogenetic grounds. Sargentini et al. (2018) reports a screen for genes involved in radiation survival of E. coli, mentioning yhjV among the genes identified.

Despite these and other progresses in the art, however, there is a need for recombinant cells and their use in methods providing for cost-effective production of melatonin, 5HTP and other desirable bioproducts. So, one object of the invention is to identify transporters useful for engineering cells towards improved export of melatonin, 5HTP and other indole-derivatives.

SUMMARY OF THE INVENTION

In a first aspect, the present invention relates to a recombinant cell comprising a biosynthetic pathway for producing an indole-derivative selected from melatonin, N-acetylserotonin, serotonin and 5-hydroxytryptophan (5HTP), wherein the recombinant cell is genetically modified to overexpress a gene encoding an integral membrane protein selected from YhjV (SEQ ID NO:2), GarP (SEQ ID NO:4), ArgO (SEQ ID NO:6), AcrAB (SEQ ID NOS:10 and 12) and LysP (SEQ ID NO:8), a functionally active variant and/or fragment of any thereof, or a combination of any two or more thereof, and wherein the amino acid sequence of the variant has a sequence identity of at least about 80% to the amino acid sequence of the integral membrane protein and the fragment comprises at least about 80% of the amino acid sequence of the integral membrane protein.

In some embodiments, the recombinant cell overexpresses a gene encoding YhjV, GarP, ArgO or AcrAB, or a combination of any two or more thereof.

In some embodiments, the recombinant cell overexpresses a gene encoding YhjV or a functionally active variant thereof.

In some embodiments, the biosynthetic pathway comprises (a) an L-tryptophan hydroxylase; (b) an L-tryptophan hydroxylase and a 5HTP decarboxylase; (c) an L-tryptophan hydroxylase, a 5HTP decarboxylase, and a serotonin acetyltransferase; (d) an L-tryptophan hydroxylase, a 5HTP decarboxylase, a serotonin acetyltransferase and an acetylserotonin O-methyltransferase; (e) a tryptophan decarboxylase and a tryptamine 5-hydroxylase; (f) a tryptophan decarboxylase; a tryptamine 5-hydroxylase, and a serotonin acetyltransferase; or (g) a tryptophan decarboxylase; a tryptamine 5-hydroxylase, a serotonin acetyltransferase and an acetyl-serotonin O-methyltransferase.

In some embodiments, the overexpression of the gene encoding the integral membrane protein provides for an increased production of the indole-derivative, an increased tolerance to the indole-derivative, or both, by the recombinant cell as compared to a non-modified control cell.

In a second aspect, the invention relates to a recombinant cell capable of producing a second indole-derivative from a first indole-derivative via a biosynthetic pathway, wherein the recombinant cell is genetically modified to overexpress a gene encoding YhjV (SEQ ID NO:2), or a functionally active variant and/or fragment thereof, wherein the amino acid sequence of the variant has a sequence identity of at least about 80% to SEQ ID NO:2 and the fragment comprises at least about 80% of SEQ ID NO:2.

In some embodiments, the recombinant cell overexpresses a gene encoding YhjV or a functionally active variant thereof. In some embodiments, the first and second indole-derivatives are: (a) tryptophan and melatonin, respectively; (b) tryptophan and N-acetylserotonin, respectively; (c) tryptophan and serotonin, respectively; and (d) tryptophan and 5-hydroxytryptophan, respectively.

In some embodiments, the overexpression of the gene encoding YhjV or the functionally active variant and/or fragment thereof provides for an increased production of the second indole-derivative, an increased tolerance to the second indole-derivative, or both, by the recombinant cell as compared to a non-modified control cell.

In some embodiments, the recombinant cell according to any aspect or embodiment herein, the integral membrane protein is expressed from a transgene or from an upregulated endogenous gene. In some embodiments, at least one of the enzymes of the biosynthetic pathway is expressed from a transgene, optionally a heterologous transgene. In some embodiments, the recombinant cell is a bacterial cell, a yeast cell, a filamentous fungal cell, an algal cell or a mammalian cell. In some embodiments, the recombinant cell is a bacterial cell, optionally of the family Enterobacteriaceae, such as an *Escherichia coli* cell.

In a third aspect, the invention relates to a method for producing an indole-derivative selected from melatonin, N-acetylserotonin, serotonin and 5HTP, comprising the step of culturing the recombinant cell according to any aspect or embodiment herein in a culture medium comprising a carbon source, and optionally, isolating the indole-derivative. In some embodiments, the medium further comprises tryptophan.

In a fourth aspect, the invention relates to a method for producing a second indole-derivative from a first indole-derivative, comprising the step of culturing the recombinant cell of any aspects or embodiment herein in a culture medium comprising a carbon source and the first indole-derivative, and optionally, isolating the second indole-derivative. In some embodiments, the first and second indole-derivatives are tryptophan and melatonin, respectively.

In a fifth aspect, the invention provides for functionally active variants or fragments of the integral membrane proteins described herein. For example, in one embodiment, the invention provides for a functionally active variant or fragment of YhjV (SEQ ID NO:2) having a sequence identity of at least about 70%, such as at least about 80%, such as at least 84%, such as at least 85%, such as at least 87%, such as at least about 90%, such as at least about 93%, such as at least about 95%, such as at least about 96%, such as at least about 97%, such as at least about 98%, such as at least about 99% to SEQ ID NO:2 or a portion thereof and comprising one or more mutations, optionally an amino acid substitution in one or more residues selected from V176, G108, I151, I182, F187, A260, C78, A260, P385, 155, N186, S268, S75 and K402. In a particular embodiment, the variant comprises a V176M, G108W, A260V, F187L, I182T, I151F, C78S, A260T, P385T, I55F, N186K, S268N, S75R or K402I amino acid substitution, such as a V176M, G108W, A260V, F187L, I182T or I151F amino acid substitution, or a combination of two or more such amino acid substitutions. In one embodiment, the invention provides for a fragment of GarP (SEQ ID NO:4), the fragment comprising or consisting of amino acid residues 1-134 of SEQ ID NO:4.

These and other aspects and embodiments are described in more detail below.

FIGURE LEGENDS

FIG. 1. Metabolic pathways for the production of melatonin, serotonin, N-acetylserotonin, and/or 5HTP. TRP=L-tryptophan; Met=methionine; SAM=S-adenosyl methionine; SAH=S-adenosyl homocysteine.

Figure 2:
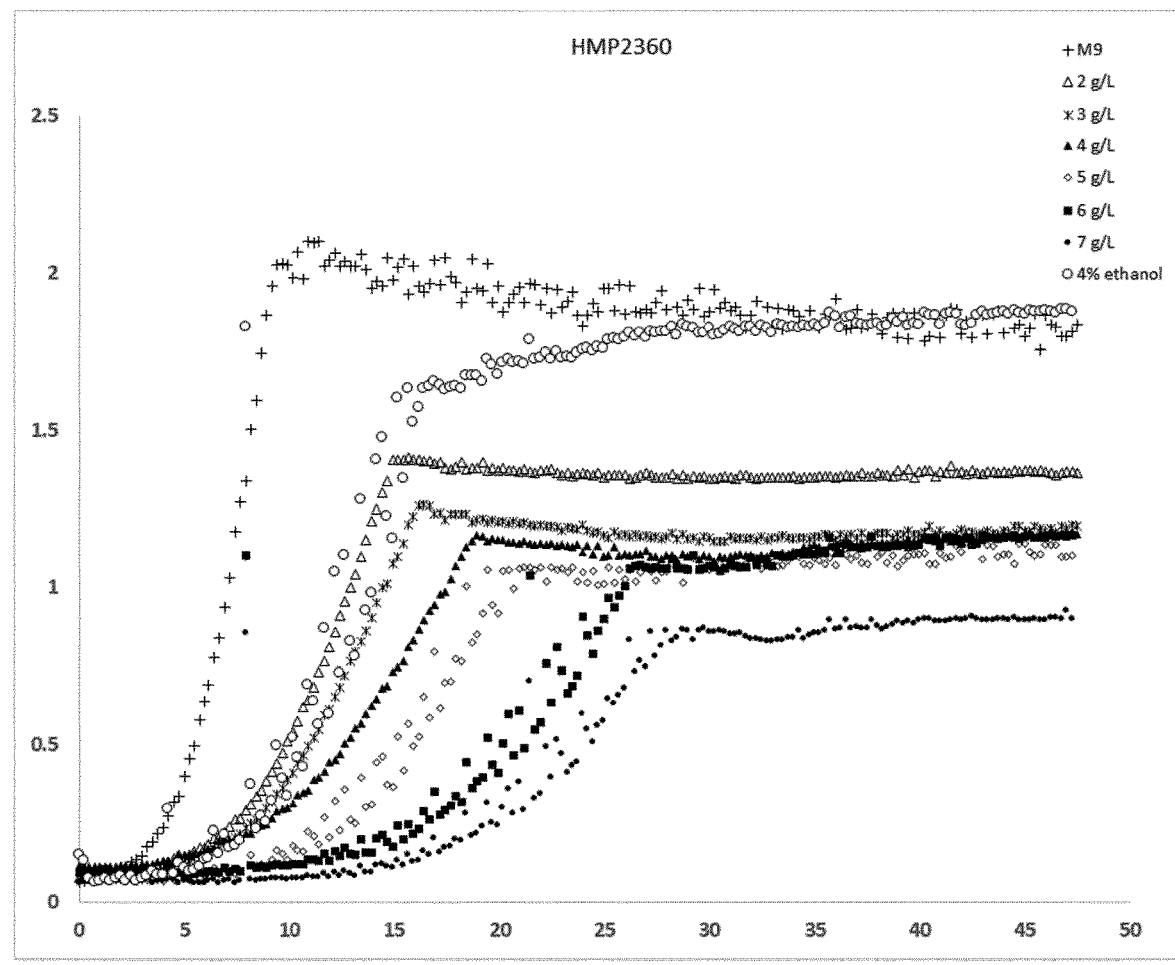

FIG. 2. High-concentration of melatonin decreased cell growth of *E. coli*. Melatonin stock-solution was made by dissolving melatonin into 70% ethanol (ETOH). The growth medium was M9 supplemented with 0.2% glucose and 2 to 7 g/L melatonin. Note that the control condition contains 4% ETOH to be comparable with growth in melatonin. The ordinate scale reflects optical density.

Figure 3:
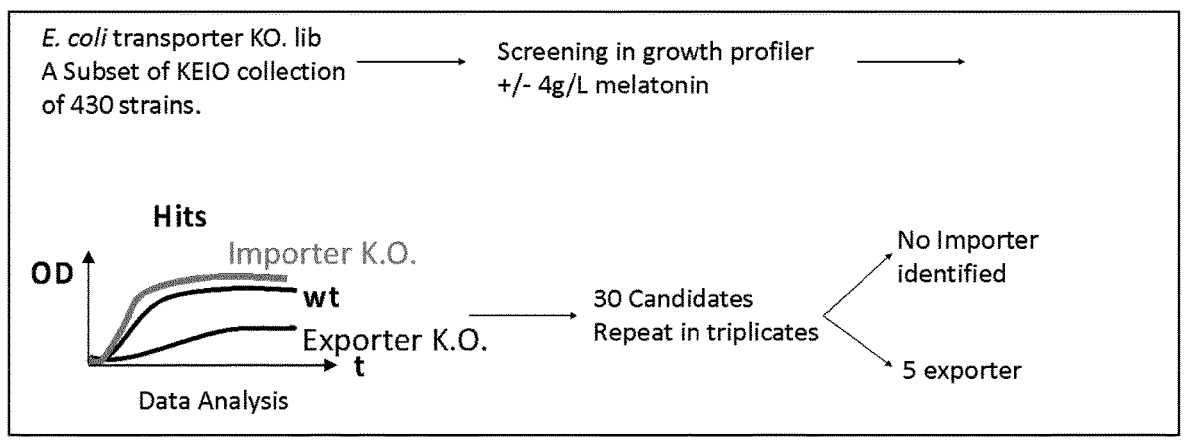
Figure 4A:
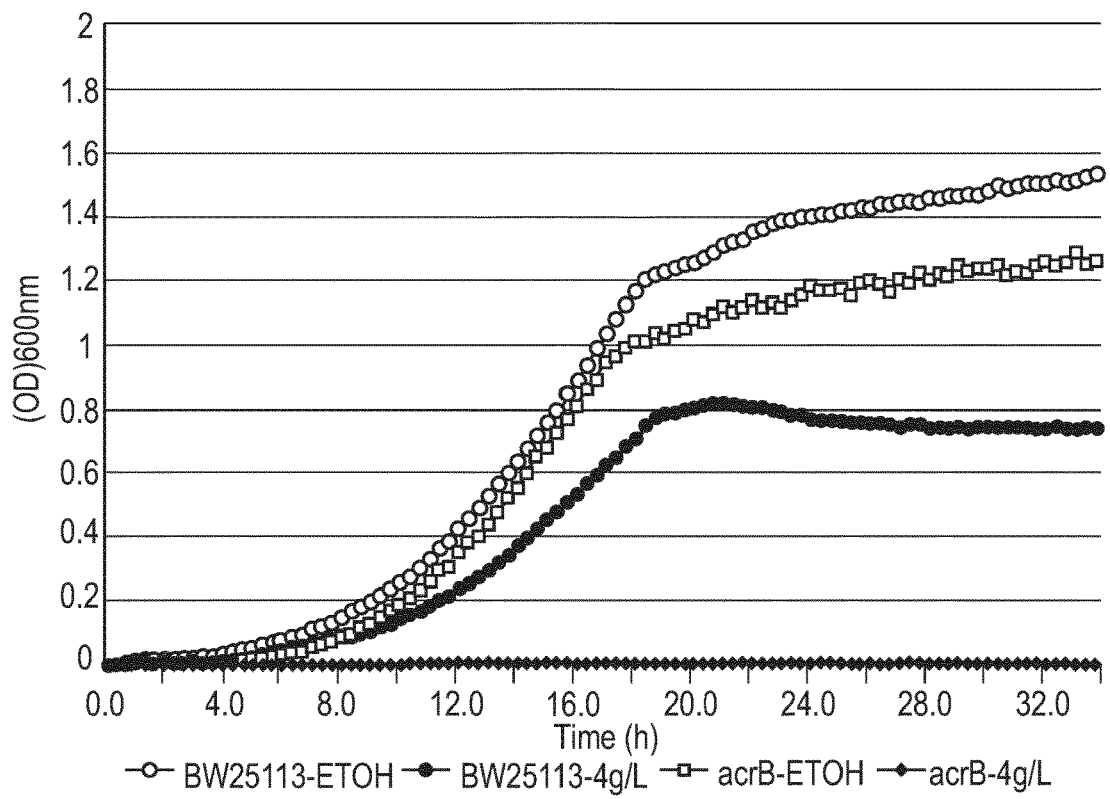
Figure 4B:
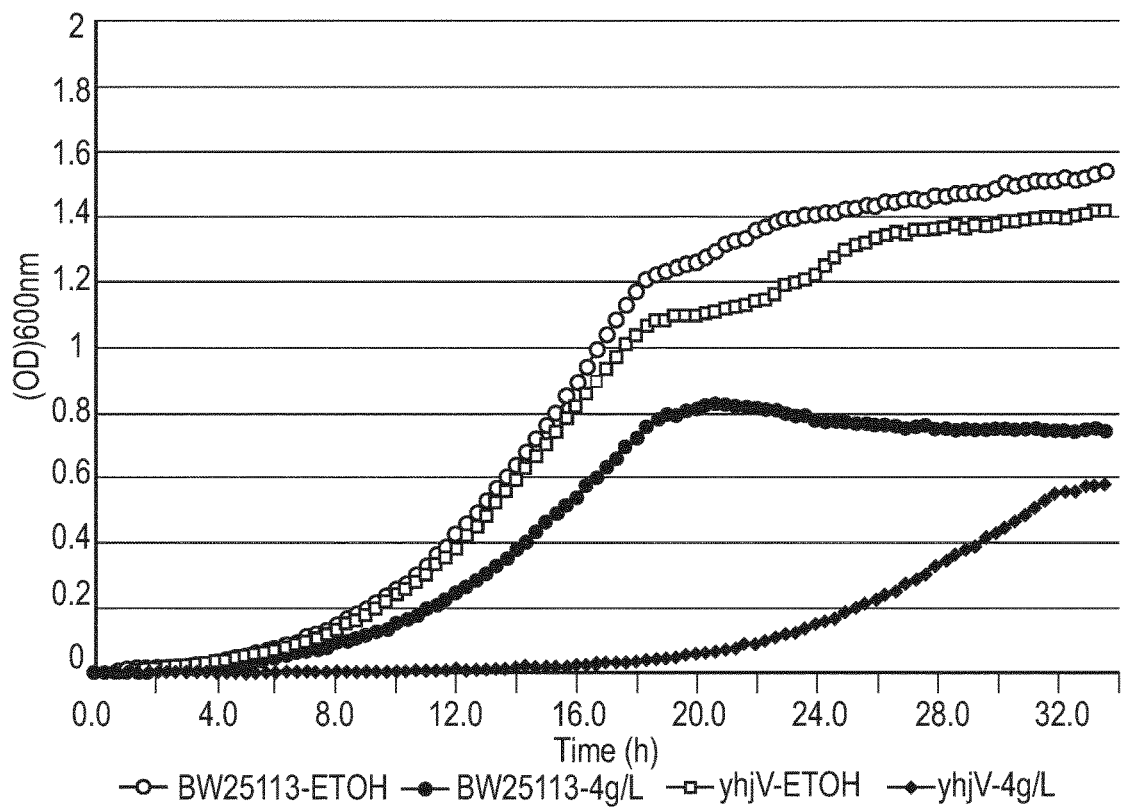
Figure 4C:
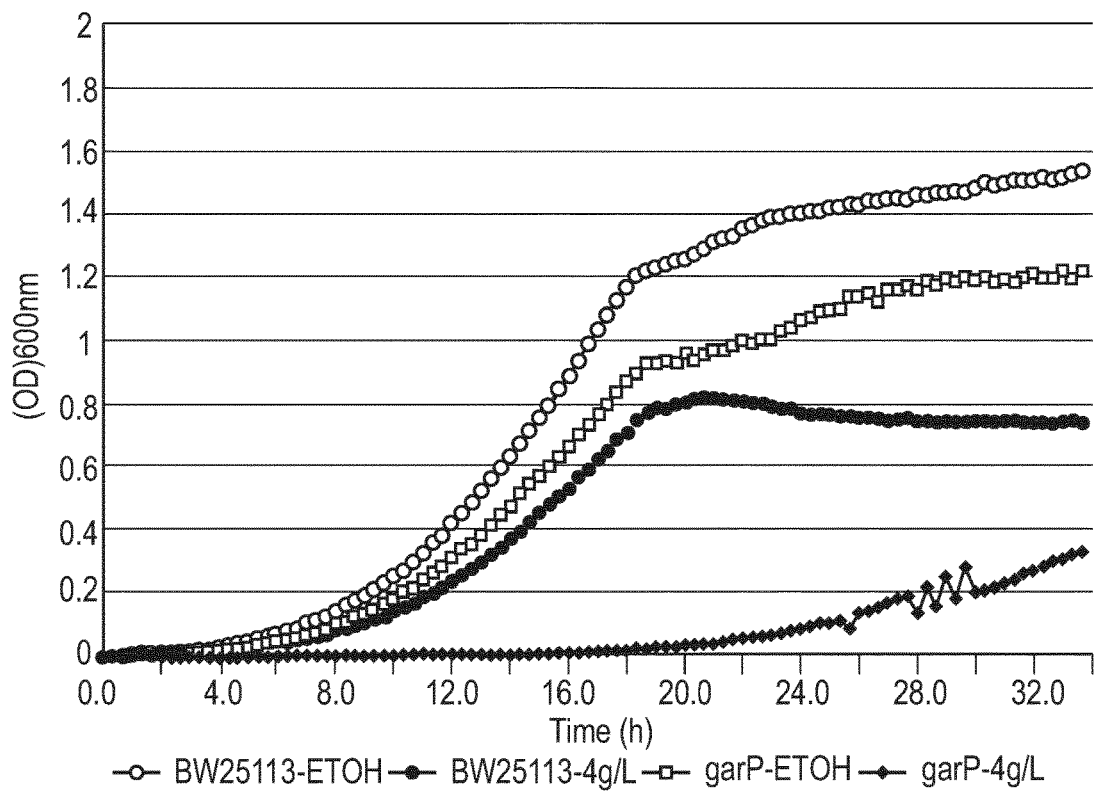
Figure 4D:
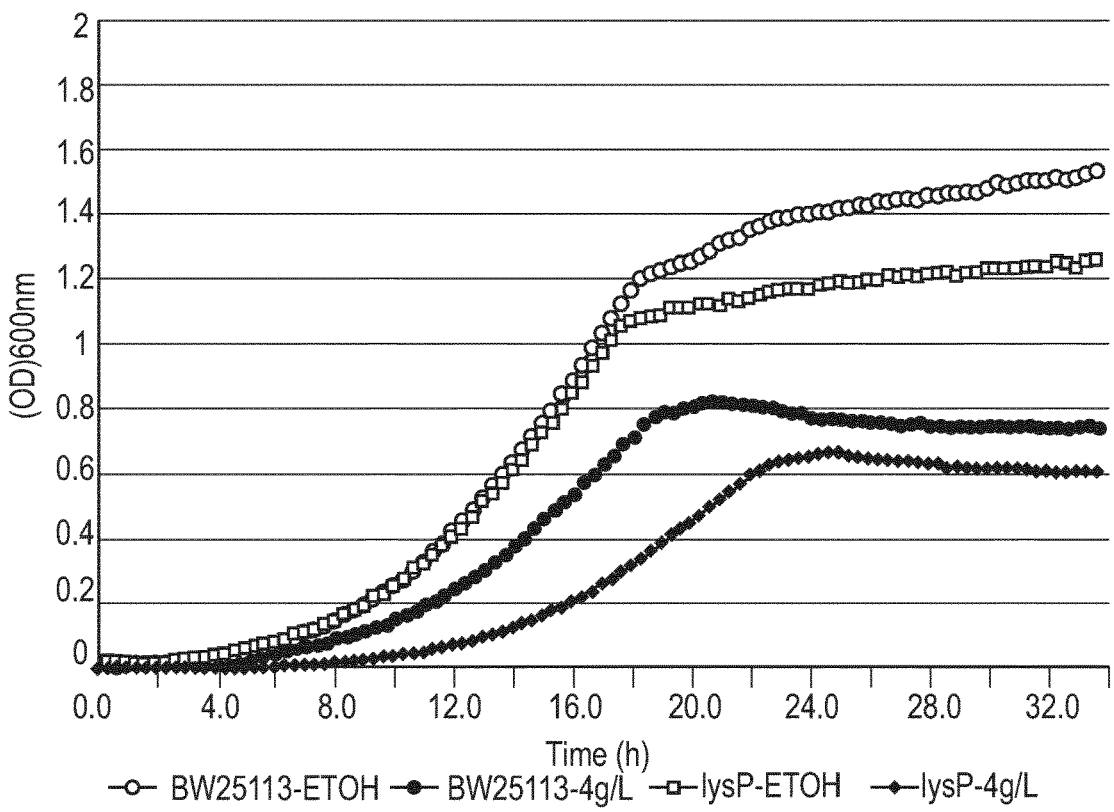
Figure 4E:
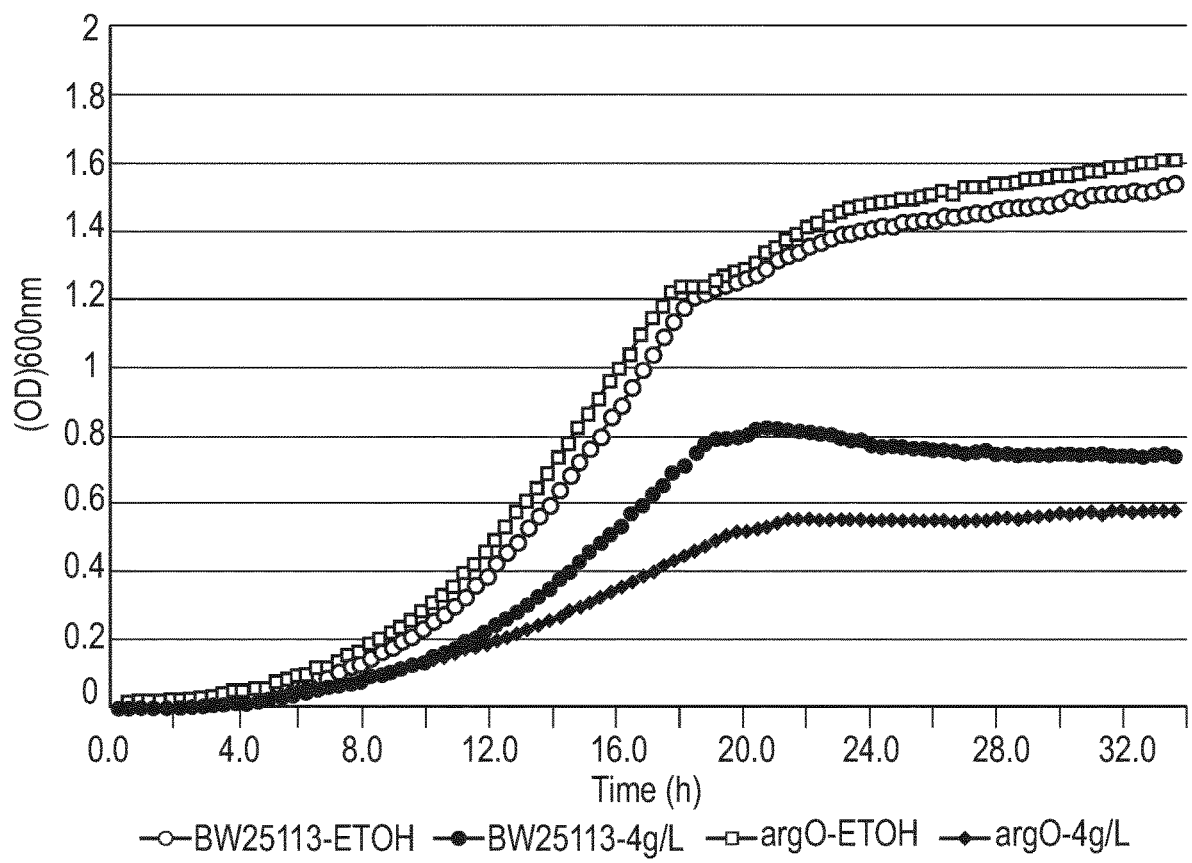

FIG. 3. Workflow for screening a transporter knockout library to identify melatonin transporters. See Example 1 for details.

FIG. 4. Growth profiles of *E. coli* BW25113 and knockout strains in the presence of 4 g/L of melatonin. (A) acrB; (B) yhjV; (C) garP; (D) lysP; (E) argO. Note that the control condition contains 4% ETOH to be comparable with growth in melatonin.

Figure 5:
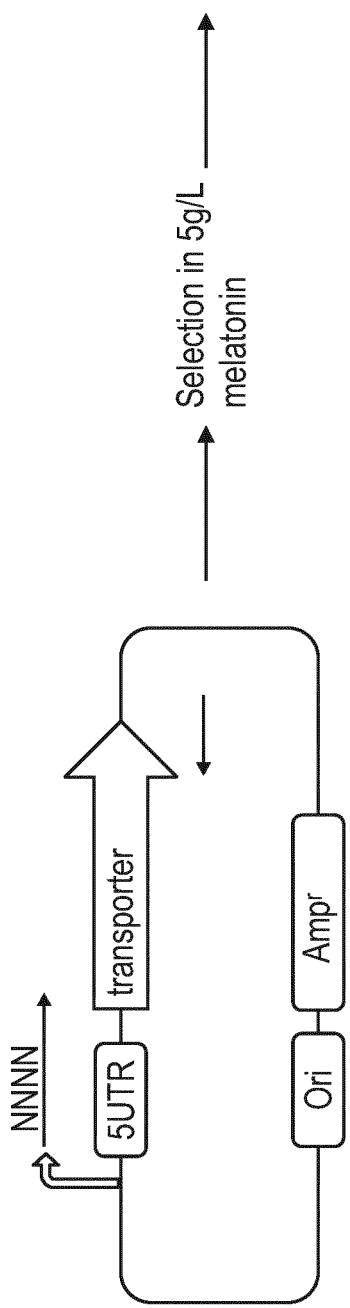
Figure 5:
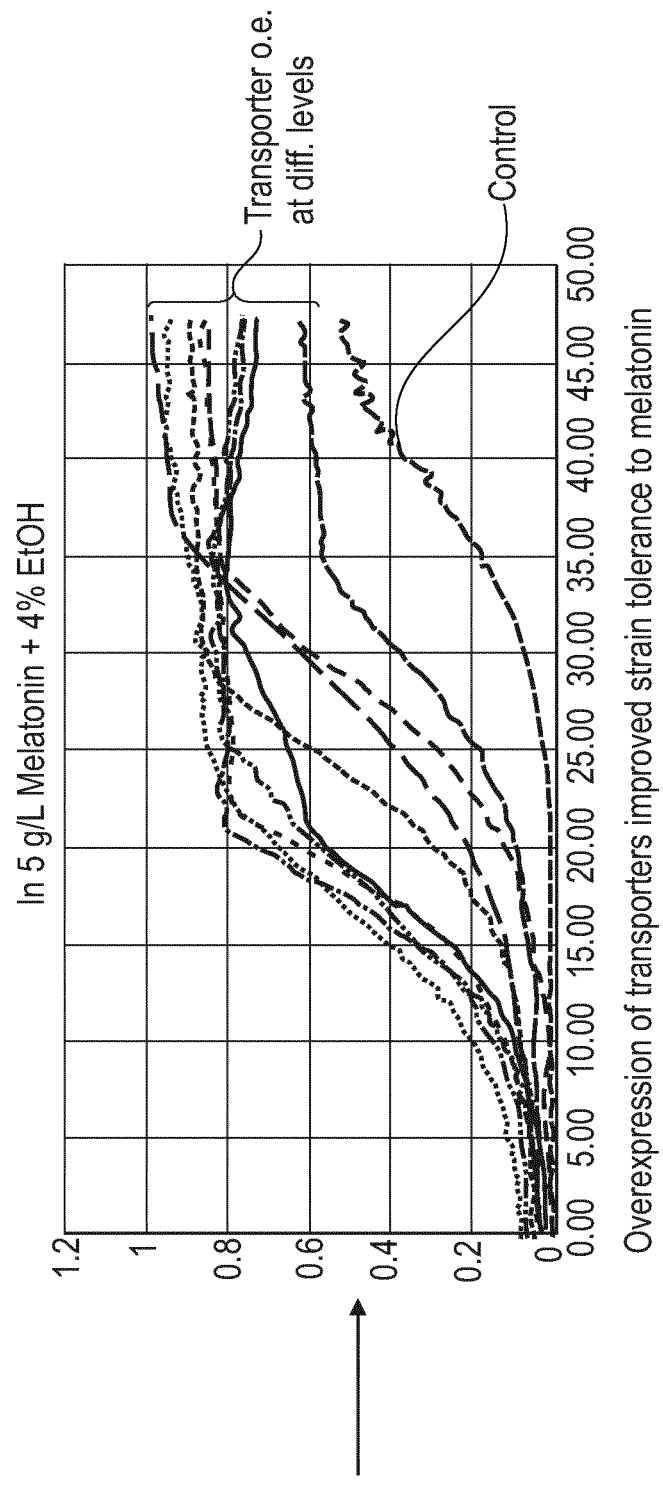

FIG. 5. Workflow for transporter overexpression ("o.e." means "overexpressed"; "diff." means "different").

Figure 6:
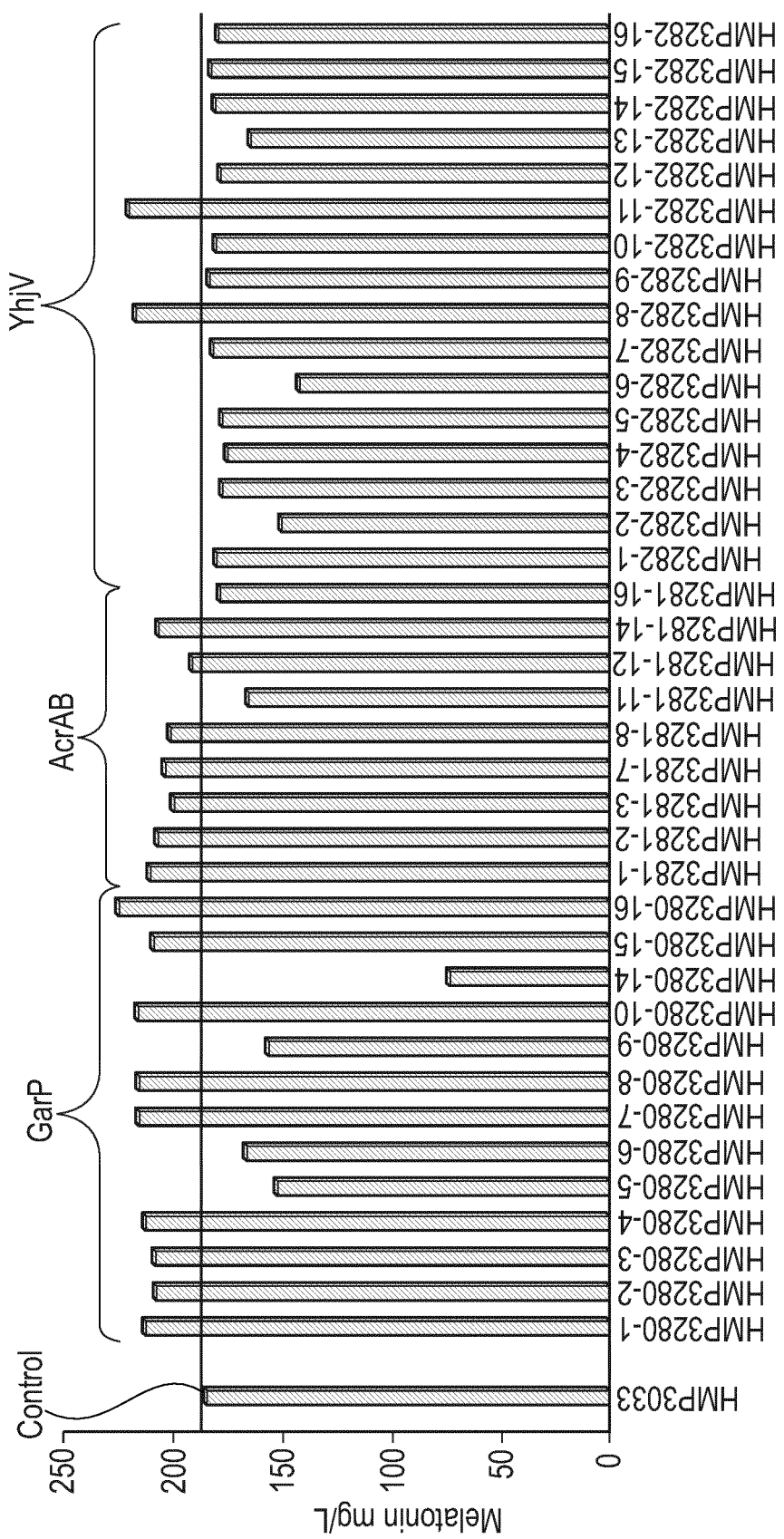
Figure 6:
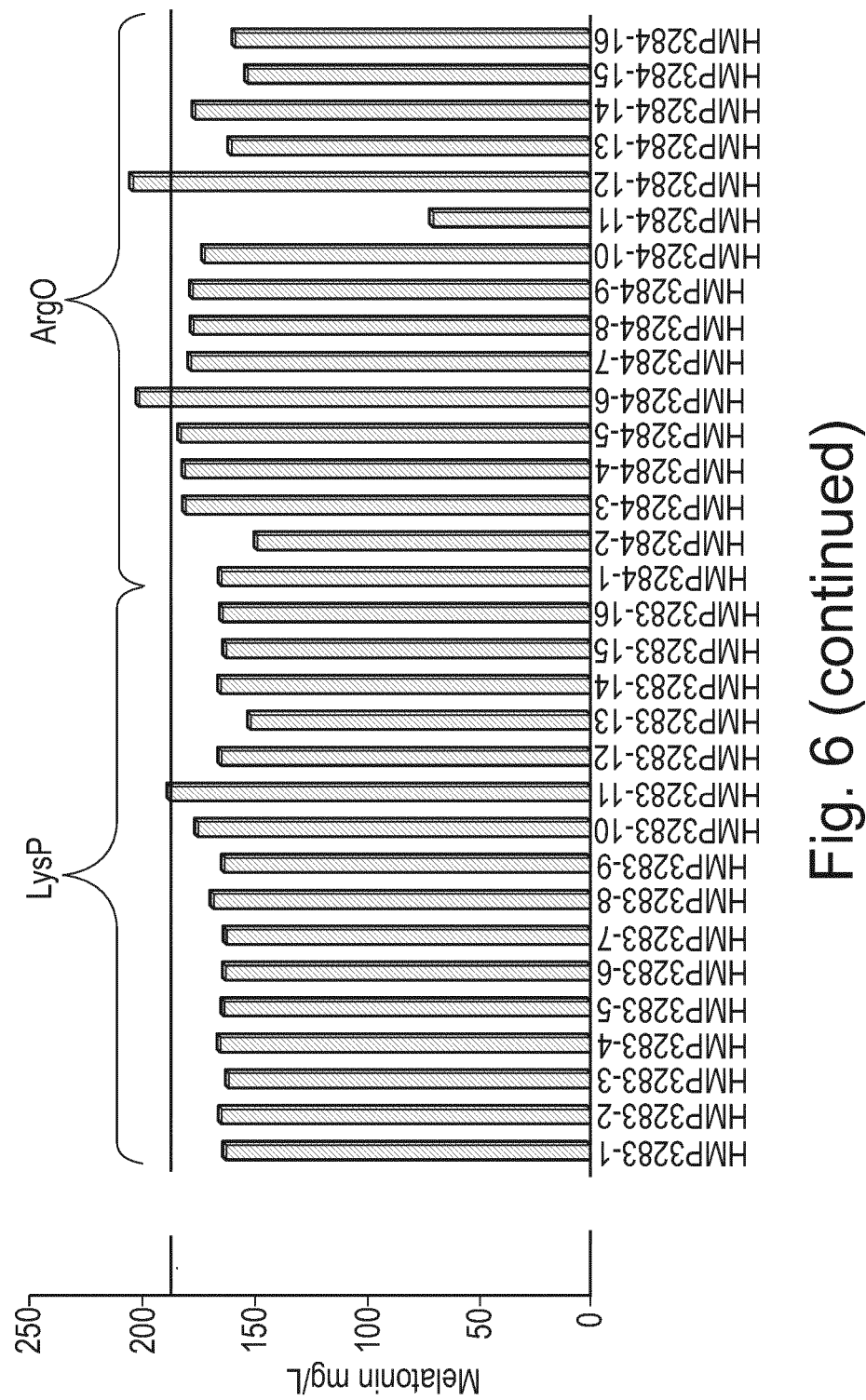

FIG. 6. Melatonin production in small scale assay with glucose and tryptophan feeding. Black bar: control strains without transporter overexpression.

Figure 7:
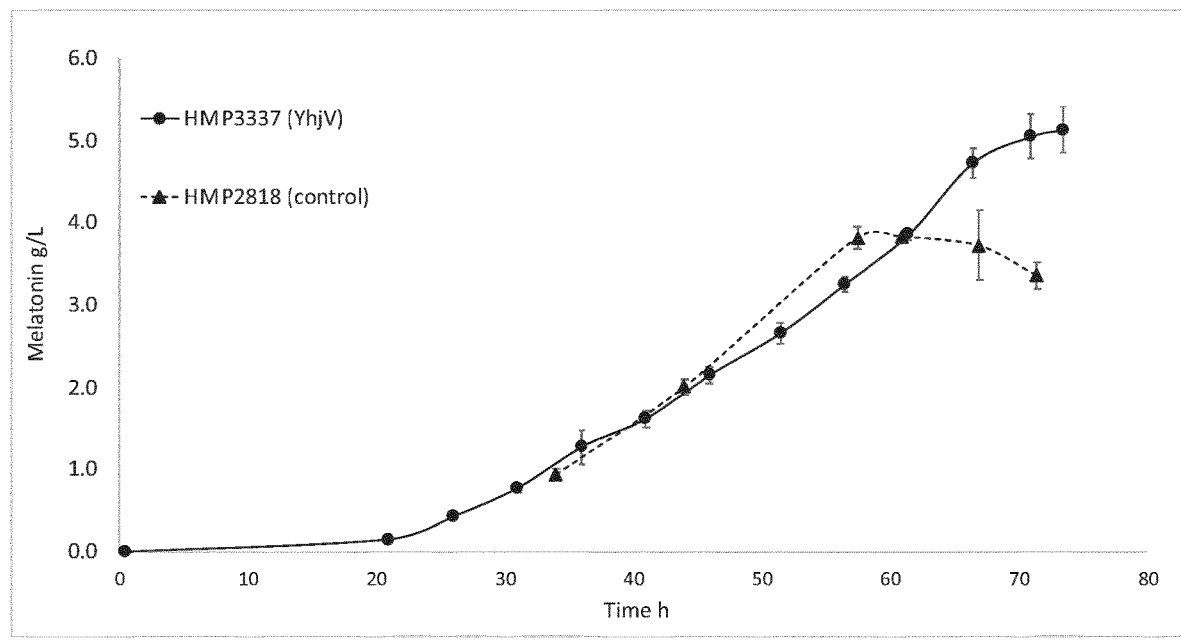
Figure 7:
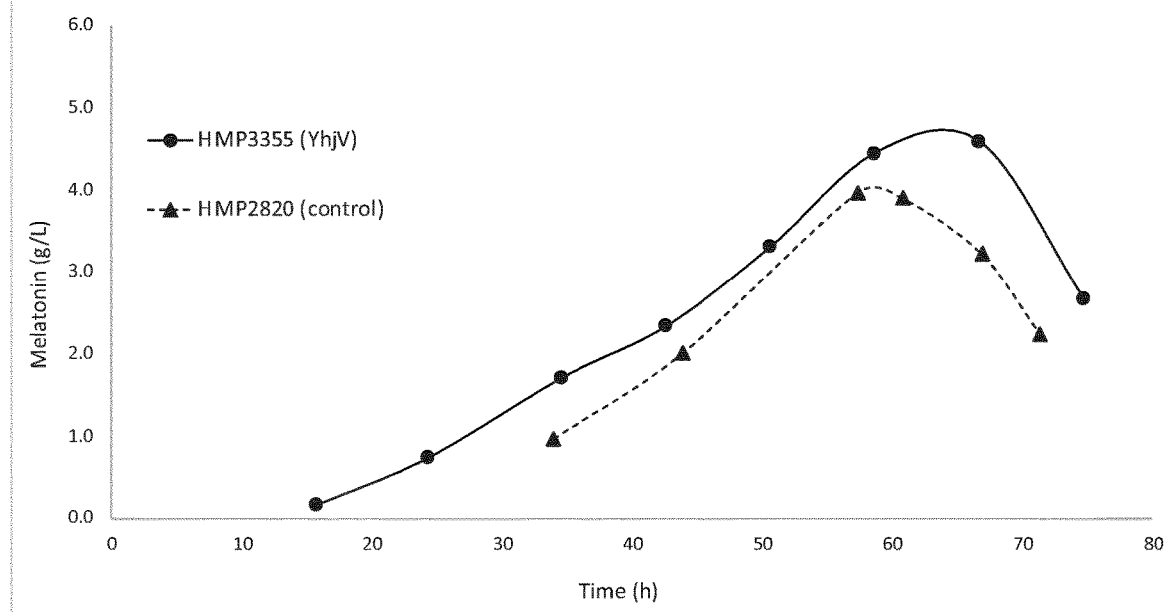
Figure 7:
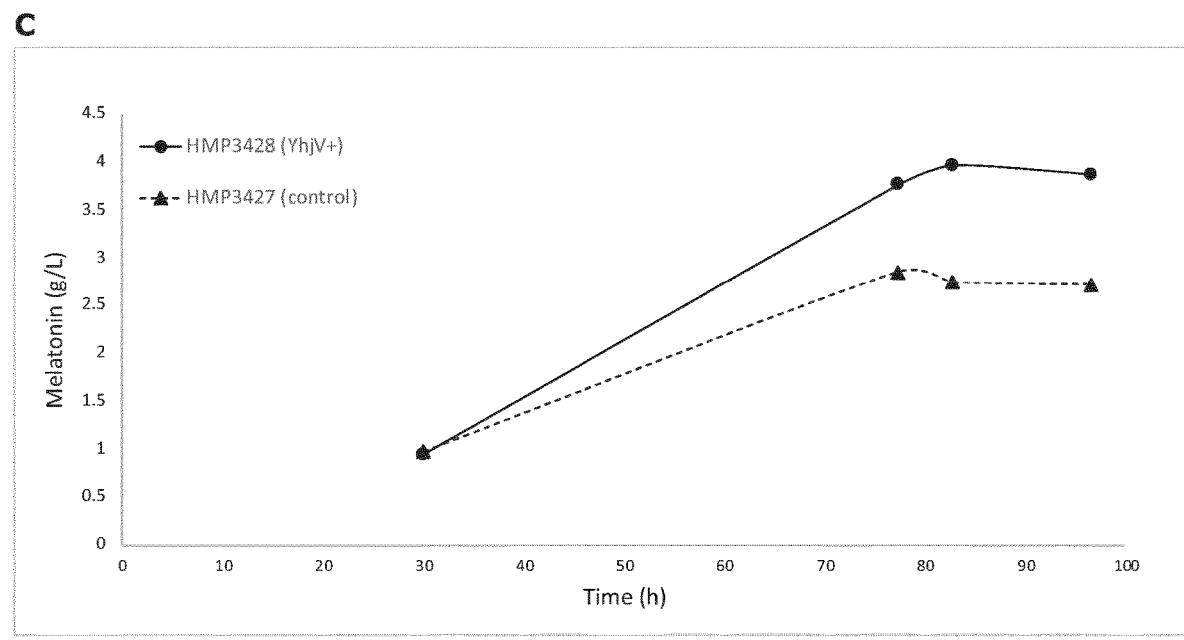

FIG. 7. Melatonin production in fed-batch fermentation with glucose and tryptophan feeding. Strains HMP3337 (YhjV overexpression) and HMP2818 (control) (A) as well as strains HMP3355 (YhjV overexpression) and HMP2820 (control) (B) were tested with glucose and tryptophan feeding. A and B represent two different strain backgrounds. Strains HMP3428 (YhjV+) and HMP3427 (control) (C) were tested with glucose feeding only.

Figure 8:
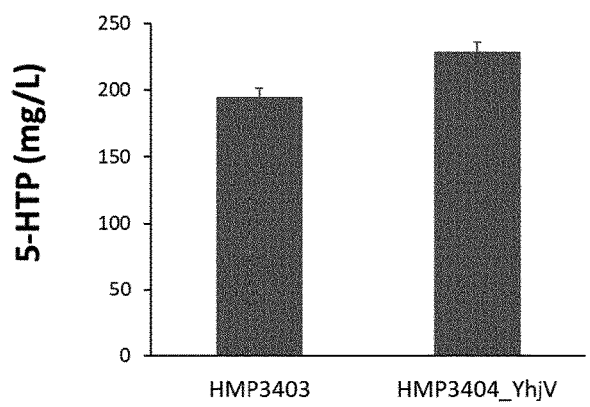

FIG. 8. 5HTP production in a small-scale assay with glucose and tryptophan feeding.

Figure 9:
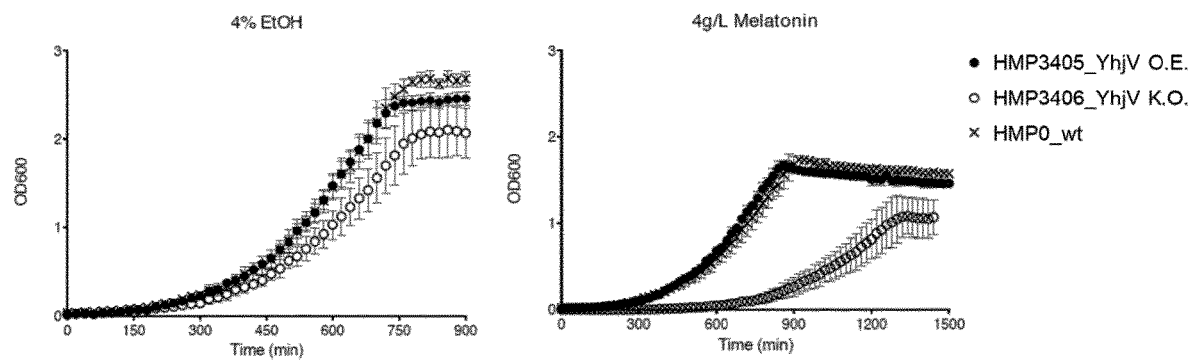

FIG. 9. Complementation of yhjV gene restored growth defect of yhjV knockout strain in melatonin.

Figure 10:
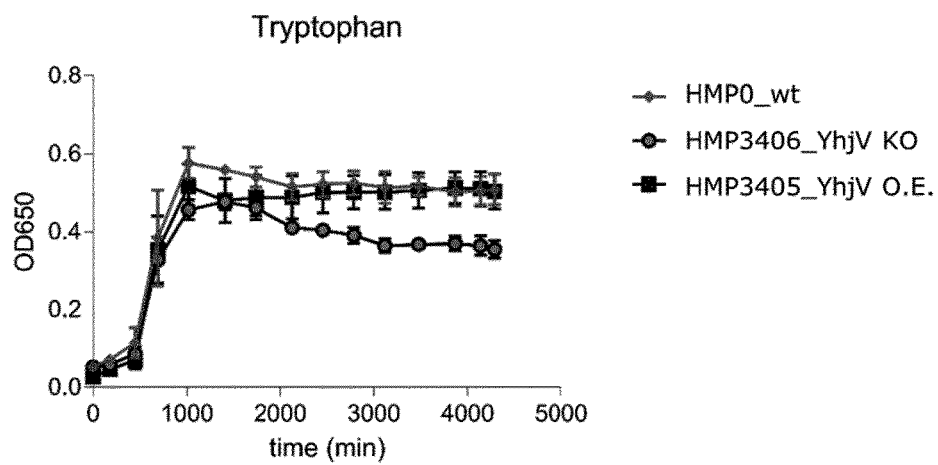

FIG. 10. Knockout of yhjV gene negatively affects *E. coli* growth in tryptophan.

Figure 11:
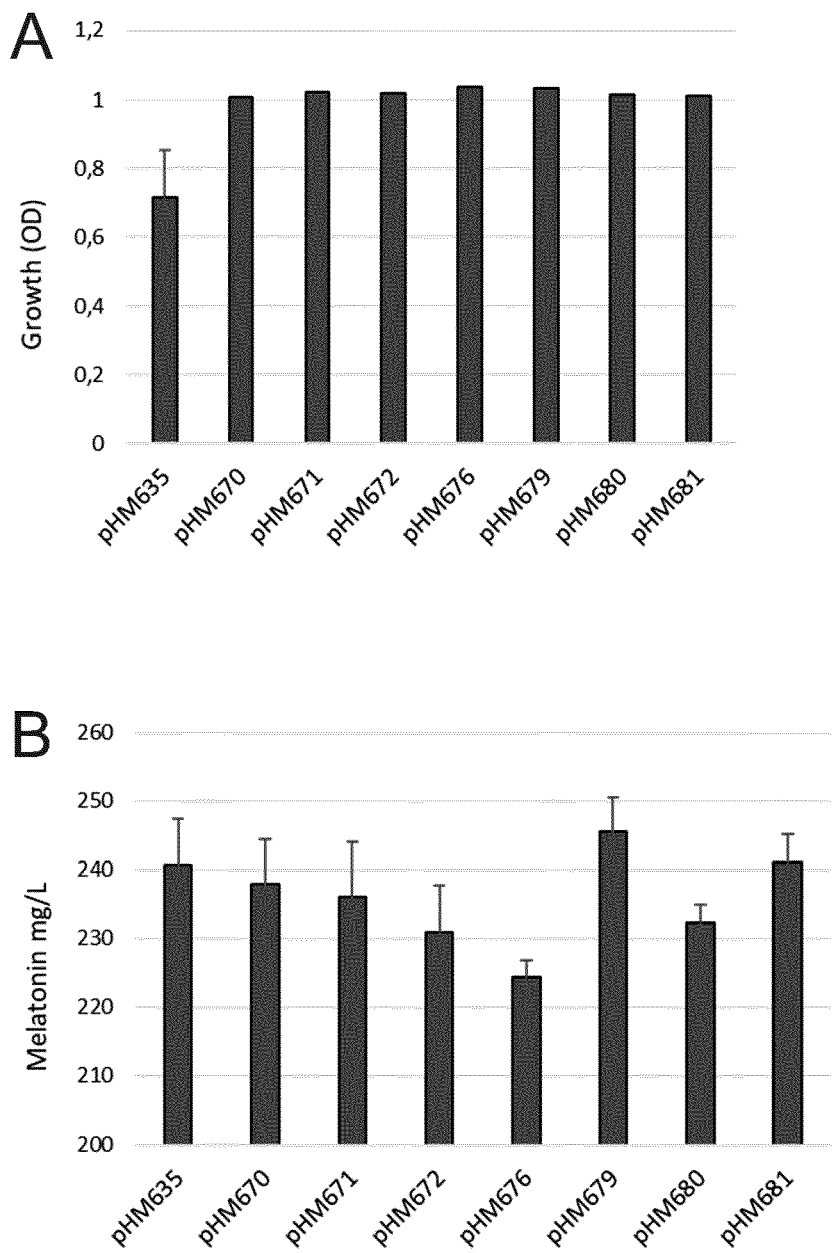

FIG. 11. Selected YhjV mutants that improved melatonin tolerance. Strain containing mutants gave rise to growth (gained biomass after 48 h of cultivation) benefit in melatonin (A). One of them also increased melatonin titer in a small-scale production assay (B). pHM635 is the control plasmid that contains the wild-type YhjV protein sequence. Error bars indicate standard deviation of 3 replicates.

DETAILED DISCLOSURE OF THE INVENTION

Definitions

Unless otherwise indicated or contradicted by context, an "indole-derivative" as used herein is a compound which comprises, as part of its chemical structure, an indole group according to Formula I, wherein each of $R_1$ to $R_7$ designates hydrogen (H) or a substituent at the indicated position, e.g., independently selected from hydrogen, an alkyl group, an alkylaryl group, a substituted alkyl group, a substituted alkylaryl group, a hydroxyl group, an amino group, a carboxyl group, a carboxylic acid group, or an ester group. In some embodiments, $R_5$ is not H. In some embodiments, $R_3$ is not H. In some embodiments, $R_3$ and $R_5$ are not H. In some preferred embodiments, $R_1$, $R_2$, $R_4$, $R_6$, and $R_7$ are H. Non-limiting examples of indole-derivatives include melatonin, N-acetylserotonin, serotonin, 5HTP, L-tryptophan, indoxyl, indican, indigo, indole-3-acetic acid (IAA), 5,6-dihydroxyindole-2-carboxylate (DHICA), tryptamine, Indometacin (2-[1-(4-chlorobenzoyl)-5-methoxy-2-methylindol-3-yl]acetic acid), Almotriptan (N,N-dimethyl-2-[5-(pyrrolidin-1-ylsulfonylmethyl)-1H-indol-3-yl] ethanamine), Bopindolol ([1-(tert-butylamino)-3-[(2-methyl-1H-indol-4-yl)oxy]propan-2-yl] benzoate), Frovatriptan ((6R)-6-(methylamino)-6,7,8,9-tetrahydro-5H-carbazole-3-carboxamide) and Zolmitriptan ((4S)-4-[[3-[2-(dimethylamino)ethyl]-1H-indol-5-yl]methyl]-1,3-oxazolidin-2-one). In one preferred embodiment, an indole-derivative is a compound having the general chemical structure of Formula I, wherein $R_5$ is OH or O—$CH_3$ and $R_3$ is $CH_2CH_2N(H)C(=O)CH_3$ or $CH_2CH_2NH_2$ or $CH_2CH_2(NH_2)COOH$. Particularly preferred indole-derivatives are melatonin, N-acetylserotonin, serotonin, 5HTP and tryptamine.

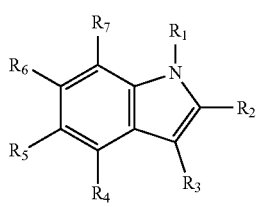

(I)

A "recombinant cell" or "a recombinant host cell" as used herein refers to a cell which has been genetically modified, e.g., to introduce one or more transgenes, typically via transformation of a host cell with a vector, or to upregulate or downregulate one or more endogenous genes.

As used herein, a "biosynthetic pathway" for a compound of interest refers to an enzymatic pathway resulting in the production of the compound in a host cell. In some embodiments, at least one of the enzymes is expressed from a transgene, i.e., a gene added to the host cell genome by transformation or other means. In such cases, the biosynthetic pathway may be referred to as a "recombinant biosynthetic pathway" or a "heterologous biosynthetic pathway." In some cases, the recombinant biosynthetic pathway also comprises a deletion of one or more native genes in the host cell. The compound of interest is typically an indole-derivative, and may be the actual end product or a precursor or intermediate in the production of another end product.

The term "substrate" or "precursor", as used herein in relation to a specific enzyme, refers to a molecule upon which the enzyme acts to form a product. When used in relation to a biosynthetic pathway, the term "substrate" or "precursor" refers to the molecule(s) upon which the first enzyme of the referenced pathway acts. When referring to an enzyme-catalyzed reaction in a cell, an "endogenous" substrate or precursor is a molecule which is native to or biosynthesized by the microbial cell, whereas an "exogenous" substrate or precursor is a molecule which is added to the microbial cell, via a medium or the like.

The term "gene" refers to a nucleic acid sequence that encodes a cellular function, such as a protein, optionally including regulatory sequences preceding (5' non-coding sequences) and following (3' non-coding sequences) the coding sequence. An "endogenous gene" refers to a native gene in its natural location in the genome of an organism. A "transgene" is a gene, native or heterologous, that has been introduced into a cell, either by natural uptake or by a genetic engineering technique, e.g., a transformation, trans- duction, or transduction procedure. Gene names are herein set forth in italicised text with a lower-case first letter (e.g., yhjV) whereas protein names are set forth in normal text with a capital first letter (e.g., YhjV).

The term "heterologous", when used to characterize a gene or protein with respect to a host cell or species, refers to a gene or protein which has a nucleic acid or amino acid sequence not normally found in the host cell or species.

As used herein, the terms "native" or "endogenous", when used to characterize a gene or protein with respect to a host cell or species, refer to a gene or protein normally found in the host cell or microbial species in question.

As used herein the term "transformation" refers to the transfer of a nucleic acid fragment, such as a gene, into a host cell. Host cells containing a gene introduced by transformation or a "transgene" are referred to as "transgenic" or "recombinant" or "transformed" cells.

The term "expression", as used herein, refers to the process in which a gene is transcribed into mRNA, and may optionally include the subsequent translation of the mRNA into an amino acid sequence, i.e., a protein or polypeptide.

As used herein, "reduced expression" or "downregulation" of an endogenous gene in a host cell means that the levels of the mRNA, protein and/or protein activity encoded by the gene are significantly reduced in the host cell, typically by at least 25%, such as at least 50%, such as at least 75%, such as at least 90%, such as at least 95%, as compared to a control. Typically, when the reduced expression is obtained by a genetic modification in the host cell, the control is the unmodified host cell. The knocking-out of a gene typically results in the native mRNA and functional protein encoded by the gene being completely absent from the host cell.

"Increased expression", "upregulation", "overexpressing" or the like, when used in the context of a gene, means increasing the level of protein encoded by said gene within a cell, typically by genetic modification of the cell. This can be determined by, e.g., comparing the level of the protein, level of mRNA encoding the protein, or the activity provided by the protein, in the genetically modified cell to that in a non-modified control (or parent) cell. Overexpression can, for example, result in an increase of the protein activity or protein or mRNA level by at least about 5%, such as at least about 10%, such as at least about 20%, such as at least about 30%, such as at least about 50%, such as at least about 100% or more. Overexpression of a gene can, for example, be achieved by placing the gene under the control of a promoter, optionally tuning the (over)expression by use of degenerate sequences in ribosome binding sites (RBSs) or other expression control sequences to obtain a diversity of expression levels and then testing for the desired protein activity or protein/mRNA level. Non-limiting examples of strong promoters suitable for, e.g., $E.\ coli$ cells are Ptrc, Plac, PlacUV5, PT7, and PTrp. Non-limiting examples of strong promoters suitable for, e.g., yeast cells are TEF1, PGK1, HXT7 and TDH3.

As used herein, an "integral membrane protein" is a protein that is integrated in or permanently attached to a biological membrane, such as a cell membrane, which typically is a phospholid bilayer. An integral protein may be a "transmembrane protein", spanning the entire biological membrane. Single-pass membrane proteins cross the membrane only once, while the sequence of multi-pass membrane proteins weave in and out, crossing the membrane several times As used herein, a "transporter" is an integral membrane protein assisting in, or facilitating, the passage of a molecule across a biological membrane, such as a cell membrane. An "efflux transporter" or "exporter" for a molecule of interest is a transporter which primarily assists or facilitates the passage of the molecule across a cell membrane from an intracellular compartment (typically the cytoplasm) to an extracellular compartment. An "influx transporter" or "importer" for a molecule of interest is a transporter which primarily assists or facilitates the passage of the molecule across a cell membrane from an extracellular compartment to an intracellular compartment (typically the cytoplasm). A "symporter" is an importer or exporter which can transport two or more molecules at the same time and in the same direction across a biological membrane, e.g., functioning as a cotransporter. An "antiport transporter" or "antiporter" is a transporter which can transport two molecules at the same time in opposite directions across a biological membrane. See, e.g., Kell, 2018.

Standard recombinant DNA and molecular cloning techniques used here are well known in the art and are described by Sambrook, J., Fritsch, E. F. and Maniatis, T. Molecular Cloning: A Laboratory Manual, 4$^{th}$ ed.; Cold Spring Harbor Laboratory: Cold Spring Harbor, New York, 2012; and by Silhavy, T. J., Bennan, M. L. and Enquist, L. W. Experiments with Gene Fusions; Cold Spring Harbor Laboratory: Cold Spring Harbor, New York, 1984; and by Ausubel, F. M. et al., In Current Protocols in Molecular Biology, published by John Wiley & Sons (1995); and by Datsenko and Wanner, 2000; and by Baba et al., 2006; and by Thomason et al., 2007.

A "variant" of a parent or reference protein comprises one or more mutations, such as amino acid substitutions, insertions and deletions, as compared to the parent or reference protein. Typically, the variant has a high sequence identity to the amino acid sequence of the parent or reference protein, e.g., at least about 70%, such as at least about 80%, such as at least 84%, such as at least 85%, such as at least 87%, such as at least about 90%, such as at least about 93%, such as at least about 95%, such as at least about 96%, such as at least about 97%, such as at least about 98%, such as at least about 99%, over at least the functionally or catalytically active portion, optionally over the full length.

Unless otherwise stated, the term "sequence identity" for amino acid sequences as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences. Hence, the amino acid sequence GSTDYTQNWA will have a sequence identity of 80% with the sequence GSTGYTQAWA ($n_{dif}$=2 and $n_{ref}$=10). The sequence identity can be determined by conventional methods, e.g., Smith and Waterman (Adv. Appl. Math. 1981; 2:482), by the 'search for similarity' method of Pearson & Lipman (Proc. Natl. Acad. Sci. USA 1988; 85:2444), using the CLUSTAL W algorithm of Thompson et al. (Nucleic Acids Res 1994; 22:467380), by computerized implementations of these algorithms (GAP, BESTFIT, FASTA, and TFASTA in the Wisconsin Genetics Software Package, Genetics Computer Group), or the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), e.g., as provided at the European Bioinformatics Institute website (www.ebi.ac.uk). The BLAST algorithm (Altschul et al., (1990), Mol. Biol. 215: 403-10) for which software may be obtained through the National Center for Biotechnology Information www.ncbi.nlm.nih.gov/) may also be used. When using any of the aforementioned algorithms, the default parameters for "Window" length, gap penalty, etc., may be used.

A residue in one amino acid sequence which "corresponds to" a specific reference residue in a reference amino acid sequence is the residue which aligns with the reference residue, e.g., as determined by use of sequence alignment software described in the preceding paragraph.

A "conservative" amino acid substitution in a protein is one that does not negatively influence protein activity. Typically, a conservative substitution can be made within groups of amino acids sharing physicochemical properties, such as, e.g., basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). Most commonly, substitutions can be made between Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly.

A "fragment" of a protein comprises at least the part of the protein which is responsible for its function of interest, that is, the functionally active portion (e.g., in the case of an enzyme, its catalytically active portion). Typically, a "fragment" comprises a segment corresponding to at least about 30%, such as at least about 50%, such as at least about 60%, such as at least about 70%, such as at least about 80%, such as at least about 90%, such as at least about 95%, of the full length protein.

A "functionally active variant" or "functionally active fragment" of a protein comprises mutations and/or truncations, respectively, which do not substantially affect the function of the variant or fragment as compared to the parent or reference protein, and can substitute at least partially for the parent or reference protein in terms of the function of interest. In the case of an enzyme having a specific catalytic activity, this can also be referred to as a "catalytically active" variant or fragment. Typically, a functionally active variant and/or fragment retains, as determined by a suitable activity assay, at least 50%, such as at least 80%, such as at least 90%, such as about 100% or more, e.g., 50-150%, such as 80-120%, such as 90%410%, such as 95%-105% or more, of the activity of a parent or reference protein which does not comprise the mutations and/or truncations in question. Suitable activity assays for comparing the transport activity of variants or fragments of transporter proteins can be found in the present Examples. For example, to test the transport activity of a variant or fragment of a transporter, the growth of a recombinant cell (e.g., an *E. coli* strain) expressing a variant or fragment of the transporter can be compared with that of the parent transporter (typically the native transporter) in 4% of ethanol and 4-5 g/L of melatonin (see Examples 1 and 5). As an alternative, the transport activity of a fragment or variant of a transporter can be evaluated in a small-scale melatonin production assay as described in Examples 1, 2 and 5, preparing a recombinant cell (e.g., an *E. coli* strain) expressing the proteins and enzymes expressed by plasmid pHM345 (Table 5) as well as the fragment or variant of the transporter, and comparing the melatonin production of that recombinant cell with a corresponding recombinant cell expressing instead of the parent transporter (typically the native transporter).

Standard recombinant DNA and molecular cloning techniques useful for construction of appropriate expression vectors and other recombinant or genetic modification techniques for practising the invention, are well known in the art and are described by, e.g., Green and Sambrook, Molecular Cloning, A Laboratory Manual, Cold Spring Harbor Laboratory Press (Cold Spring Harbor, N.Y.) (2012); by Silhavy, T. J., Bennan, M. L. and Enquist, L. W. Experiments with Gene Fusions; Cold Spring Harbor Laboratory: Cold Spring Harbor, New York, 1984; by Ausubel et al., Short Protocols in Molecular Biology, Current Protocols, John Wiley and Sons (New Jersey) (2002), and references cited herein. Appropriate microbial cells and vectors are available commercially through, for example, the American Type Culture Collection (ATCC), Rockville, Md.

Enzymes referred to herein can be classified on the basis of the handbook Enzyme Nomenclature from NC-IUBMB, 1992), see also the ENZYME site at the internet: http://www.expasy.ch/enzyme/. This is a repository of information relative to the nomenclature of enzymes, and is primarily based on the recommendations of the Nomenclature Committee of the International Union of Biochemistry and Molecular Biology (IUB-MB). It describes each type of characterized enzyme for which an EC (Enzyme Commission) number has been provided (Bairoch A., The ENZYME database, 2000, Nucleic Acids Res 28:304-305). The IUBMB Enzyme nomenclature is based on the substrate specificity and occasionally on their molecular mechanism.

Specific Embodiments of the Invention

The present inventors found that melatonin is toxic to *E. coli* cell growth in high concentrations (FIG. 2). So, they identified a need to reduce the intracellular concentration of melatonin in order to support high melatonin fermentation titers and yields. They subsequently identified proteins and polypeptides capable of transporting melatonin, 5HTP, and other indole-derivatives across a biological membrane, e.g., a cell membrane.

For example, YhjV, GarP, ArgO, AcrB, and LysP were identified as transporters providing for melatonin export (Example 1). YhjV was further identified as providing for 5HTP export (Example 2) and for L-tryptophan import (Example 3). Without being limited to theory, YhjV may thus assist or facilitate both the import of tryptophan or other indole-derivatives into a cell and the export of other indole-derivatives such as melatonin and 5HTP out of the cell, optionally functioning as an antiport transporter.

The novel transporters identified can thus be beneficial for improving the tolerance of *E. coli* and other cells to higher concentrations of melatonin and other indole-derivatives. Further, the novel transporters identified may also allow for the development of cell factories for more efficient production of melatonin and other indole-derivatives via biosynthetic pathways, e.g., from a tryptophan substrate or precursor.

In particular, overexpression of the gene encoding the integral membrane protein may provide for an increased production of the indole-derivative, an increased tolerance to the indole-derivative, or both, by the recombinant cell as compared to a non-modified control cell. This can be tested according to the assays described in the present Examples.

So, in some aspects, the invention relates to cells that are genetically modified to overexpress one or more of the genes encoding the transporters indicated in Table 1, or a functionally active variant or derivative thereof.

TABLE 1

*E. coli* transporters of indole-derivatives

| Name (gene) | Description and UniProtKB reference | Sequences* |
|---|---|---|
| YhjV (yhjV) | Putative amino acid transporter; UniProtKB - P37660 (YHJV_ECOLI) | Gene: 1272 bp (SEQ ID NO: 1) Protein: 432 aa (SEQ ID NO: 2) |
| GarP (garP) | Galactarate/glucarate/glycerate transporter; UniProtKB - B1LFM8 (B1LFM8_ECOSM) | Gene: 1335 bp (SEQ ID NO: 3) Protein: 444 aa (SEQ ID NO: 4) |
| ArgO (argO) | L-arginine efflux transporter; UniProtKB - P11667 (ARGO_ECOLI) | Gene: 636 bp (SEQ ID NO: 5) Protein: 211 aa (SEQ ID NO: 6) |
| LysP (lysP) | lysine: H+ symporter; UniProtKB - P25737 (LYSP_ECOLI) | Gene: 1470 bp (SEQ ID NO: 7) Protein: 489 aa (SEQ ID NO: 8) |

TABLE 1-continued

*E. coli* transporters of indole-derivatives

| Name (gene) | Description and UniProtKB reference | Sequences* |
|---|---|---|
| AcrA (acrA) | Multidrug efflux pump subunit; UniProtKB - P0AE06 (ACRA_ECOLI) | Gene: 1194 bp (SEQ ID NO: 9) Protein: 397 aa (SEQ ID NO: 10) |
| AcrB (acrB) | Multidrug efflux pump subunit; UniProtKB - P31224 (ACRB_ECOLI) | Gene: 3150 bp (SEQ ID NO: 11) Protein: 1049 aa (SEQ ID NO: 12) |

*bp = base pairs; aa = amino acids

In some embodiments, the recombinant cell is genetically modified to overexpress a gene encoding an integral membrane protein selected from YhjV (SEQ ID NO:2), GarP (SEQ ID NO:4), ArgO (SEQ ID NO:6), AcrAB (SEQ ID NOS:10 and 12) and LysP (SEQ ID NO:8), a functionally active variant and/or fragment of any thereof, or a combination of any two or more thereof.

Functionally active fragments and variants of YhjV (SEQ ID NO:2), GarP (SEQ ID NO:4), ArgO (SEQ ID NO:6), AcrAB (SEQ ID NOS:10 and 12) and LysP (SEQ ID NO:8) can be identified by a person of skill in the art.

For example, the full-length sequence can be truncated from the N- and/or C-terminal to remove portions not necessary for its transport activity while preserving the portion of the protein responsible for its transport activity with respect to melatonin, 5HIP, L-tryptophan or other indole-derivative. For example, such a fragment may comprise at least about 30%, such as at least about 50%, such as at least about 60%, such as at least about 70%, such as at least about 80%, such as at least about 90%, such as at least about 95%, of the full length of the protein, counting by its amino acid residues in the native, full-length sequence. Alternatively, such a fragment can be obtained by removing, e.g., 1, 2, 3, 4, 5, 10, 20 or more amino acid residues from the C-terminal, N-terminal, or both.

Variants of the transporter comprising one or more amino acid substitutions, deletions or insertions can also be prepared and identified by screening or testing them for their transport activity with respect to melatonin, 5HIP, L-tryptophan or other indole-derivative, selecting variants that are functionally active. For example, such variants may have a sequence identity of at least about 70%, such as at least about 80%, such as at least 84%, such as at least 85%, such as at least 87%, such as at least about 90%, such as at least about 93%, such as at least about 95%, such as at least about 96%, such as at least about 97%, such as at least about 98%, such as at least about 99% to the native, full-length sequence or a portion thereof. Alternatively, such a variant may comprise up to 10 mutations, such as 1, 2, 3, 4, 5, 6, 7, 8, 9 or 10 mutations. In one embodiment, the variant differs from the native sequence only by conservative amino acid substitutions.

In some embodiments, the C- or N-terminal of the integral membrane protein, or functionally active variant or fragment thereof, is fused or conjugated to a second polypeptide, such as a protein tag. Suitable protein tags for facilitating detection of a protein or for improving stability, solubility or other properties of a protein are well-known in the art. Non-limiting proteins tags for facilitating protein expression include Green Fluorescent protein (GFP) and Red Fluorescent Protein (RFP).

Suitable assays for testing the transport activity of such fragments and variants are provided in Examples 1 to 3. The transport activity of the native, full-length transporter (see Table 1) can advantageously serve as a control to identify functionally active fragment and variants of the transporter in question, which typically retain at least 50%, such as at least 80%, such as 100% or more, e.g., 50-150%, such as 80-120%, such as 90%410%, such as 95%-105%, of the activity of the native, full-length transporter.

YhjV

In some embodiments, the integral membrane protein is YhjV (SEQ ID NO:2) or a functionally active variant and/or fragment thereof. YhjV is an uncharacterised protein which has earlier been assigned, based on phylogenetic grounds, to the Hydroxy/Aromatic Amino Acid Permease (HAAAP) Family within the Amino Acid-Polyamine-Organocation (APC) Superfamily. Based on its amino acid sequence, the protein has been predicted to comprise 11 transmembrane helices and a C-terminus located in the periplasm. In one preferred embodiment, the integral membrane protein is YhjV (SEQ ID NO:2).

Contemplated fragments and variants of YhjV (SEQ ID NO:2) include those exemplified above, including fragments which are N- and/or C-terminally truncated forms and variants comprising one or more amino acid substitutions, any of which may further be fused or conjugated to a second polypeptide.

In one embodiment, the variant is a functionally active fragment or variant which has a sequence identity of at least about 70%, such as at least about 80%, such as at least 84%, such as at least 85%, such as at least 87%, such as at least about 90%, such as at least about 93%, such as at least about 95%, such as at least about 96%, such as at least about 97%, such as at least about 98%, such as at least about 99% to SEQ ID NO:2 or a portion thereof and further comprises a mutation in one or more residues.

In one embodiment, at least one mutation is in a residue selected from V176, G108, I151, I182, F187, A260, C78, A260, P385, 155, N186, S268, S75 and K402. In a particular embodiment, the variant comprises a V176M, G108W, A260V, F187L, I182T, I151F, G108W, A260V, F187L, V176M, I151F, C78S, A260T, P385T, I55F, N186K, S268N, S75R or K402T amino acid substitution, or a combination of two or more such amino acid substitutions. In one embodiment, at least one mutation is in a residue selected from V176, G108, I151, I182, F187, and A260, such as in V176. In a particular embodiment, the variant comprises a V176M, G108W, A260V, F187L, I182T or I151F amino acid substitution, or a combination of two or more such amino acid substitutions. In one embodiment, at least one mutation is in a residue selected from C78, A260, P385, 155, N186, S268, S75 and K402. In a particular embodiment, the variant comprises a C78S, A260T, P385T, I55F, N186K, S268N, S75R or K4021 amino acid substitution, or a combination of two or more such amino acid substitutions. In a specific embodiment, the variant is a functionally active fragment or variant which has a sequence identity of at least about 70%, such as at least about 80%, such as at least about 84%, such as at least 85%, such as at least about 87%, such as at least about 90%, such as at least about 93%, such as at least about 95%, such as at least about 96%, such as at least about 97%, such as at least about 98%, such as at least about 99% to SEQ ID NO:2 or a portion thereof and comprises a mutation in residue V176, such as a V176M amino acid substitution.

Further contemplated are variants which are homologs or orthologs of YhjV, examples of which are shown in Table 2 below.

TABLE 2

Homologs or orthologs identified by protein BLAST (BLASTP) of *E. coli* K-12 MG1655 proteins against protein databases from selected reference organisms. "SID" refers to sequence identify to YhjV (SEQ ID NO: 2). "Sequence" refers to UniProtKB, RefSeq, or Genbank identifier.

| Protein (organism) | SID | Description | Sequence |
|---|---|---|---|
| YhaO (*E. coli*) | 45% | Serine transporter (443aa) | P42628 |
| TdcC (*E. coli*) | 23.9% | Threonine/Serine transporter (443aa) | P0AAD8 |
| SdaC (*E. coli*) | 25.3% | Serine importer (429aa) | P0AAD6 |
| YqeG (*E. coli*) | 21.5% | Amino acid transporter (409aa) | P63340 |
| (*Rodentibacter pneumotropicus*) | 47.9% | Uncharacterized Protein | WP_077664799.1 |
| (*Methanoculleus* sp. SDB) | 21% | Sodium: calcium symporter | KQC04638.1 |
| (*Citrobacter koseri*) | 88.5% | Transporter | WP_104868054.1 |
| (*Shigella sonnei* Ss046) | 100% | Putative transporter | AAZ90392.1 |

GarP

In some embodiments, the integral membrane protein is GarP (SEQ ID NO:4) or a functionally active variant and/or fragment thereof. GarP has been earlier assigned as a member of the major facilitator superfamily (MFS) of transporters, and as a galactarate/glucarate/glycerate transporter. In one preferred embodiment, the integral membrane protein is GarP (SEQ ID NO:4).

Contemplated fragments and variants of GarP (SEQ ID NO:4) include those exemplified above, including fragments which are N- and/or C-terminally truncated forms and variants comprising one or more amino acid substitutions, any of which may further be fused or conjugated to a second polypeptide.

In one embodiment, the integral membrane protein is a fragment of GarP comprising at least amino acid residues 1-130 SEQ ID NO:4, such as at least amino acid residues 1-134 of SEQ ID NO:4. In a particular embodiment, the fragment is residues 1-134 of SEQ ID NO:4, which has been shown in the Examples to be functionally active (where it is referred to as "garP(R135*)"). Variants of GarP which are fragments comprising residues 1-130, such as residues 1-134, of SEQ ID NO:4 and further comprises one or more mutations as compared to the native amino acid sequence are also specifically contemplated.

AraO

In some embodiments, the integral membrane protein is ArgO (SEQ ID NO:6) or a functionally active variant and/or fragment thereof. ArgO has been earlier assigned as a member of the LysE family of lysine efflux transporters and as a L-arginine efflux transporter, with 5 predicted transmembrane regions. Experimental topology analysis suggests that it adopts an Nin:Cout conformation. In one preferred embodiment, the integral membrane protein is ArgO (SEQ ID NO:6).

Contemplated fragments and variants of ArgO (SEQ ID NO:6) include those exemplified above, including fragments which are N- and/or C-terminally truncated forms and variants comprising one or more amino acid substitutions, any of which may further be fused or conjugated to a second polypeptide.

AcrAB

In some embodiments, the integral membrane protein is AcrAB, with the AcrA and AcrB subunits having the amino acid sequences of SEQ ID NO:10 and 12, respectively, or a functionally active variant and/or fragment of AcrAB, comprising a variant and/or fragment of AcrA, AcrB or both. AcrB, the RND (resistance-nodulation-division) family protein, is known as the inner membrane component of the tripartite, proton dependent, drug efflux pump AcrAB-ToIC. AcrB contains 12 potential transmembrane regions and two large hydrophilic domains. AcrA is the periplasmic lipoprotein component of the AcrAB-ToIC and AcrAD-ToIC multidrug efflux pumps. In one preferred embodiment, the integral membrane protein is AcrAB, with the AcrA and AcrB subunits having the amino acid sequences of SEQ ID NO:10 and 12, respectively.

Contemplated fragments and variants of AcrAB include those exemplified above, including fragments which comprise N- and/or C-terminally truncated forms and variants of AcrA (SEQ ID NO:10), AcrB (SEQ ID NO:12) or both and variants comprising one or more amino acid substitutions in AcrA, AcrB or both, any of which may be fused or conjugated to a second polypeptide. In a particular embodiment, fragments and variants of AcrAB include fragments which comprise N- and/or C-terminally truncated forms or variants of AcrB (SEQ ID NO:12) and variants comprising one or more amino acid substitutions, any of which may be fused or conjugated to a second polypeptide.

LysP

In some embodiments, the integral membrane protein is LysP (SEQ ID NO:8) or a functionally active variant and/or fragment thereof. LysP has been earlier assigned as a lysine-specific permease, with 12 transmembrane segments. In one preferred embodiment, the integral membrane protein is LysP (SEQ ID NO:8).

Contemplated fragments and variants of LysP (SEQ ID NO:8) include those exemplified above, including fragments which are N- and/or C-terminally truncated forms and variants comprising one or more amino acid substitutions, any of which may further be fused or conjugated to a second polypeptide.

Biosynthetic Pathways

Preferably, the recombinant cell comprises a biosynthetic pathway for producing one or more indole-derivatives, most preferably melatonin, N-acetylserotonin, serotonin and/or 5HTP, and typically from an L-tryptophan precursor or substrate.

For production of 5HTP, the biosynthetic pathway may comprise an L-tryptophan hydroxylase (TPH), catalyzing the conversion of L-tryptophan into 5HTP. For production of serotonin, the biosynthetic pathway may further comprise a 5HTP decarboxylase (DDC), catalyzing the conversion of 5HTP to serotonin. For production of N-acetylserotonin, the biosynthetic pathway may further comprise a serotonin acetyltransferase (AANAT), catalyzing the conversion of serotonin to N-acetylserotonin. For production of melatonin, the biosynthetic pathway may further comprise an acetylserotonin O-methyltransferase (ASMT), catalyzing the conversion of N-acetylserotonin to melatonin.

The enzymes of the biosynthetic pathway may be endogenous to the cell. For example, at least in vertebrates, melatonin is biosynthesized via the Shikimate pathway from the native precursor L-tryptophan (FIG. 1). Accordingly, in embodiments where the recombinant cell is a vertebrate cell, e.g., a mammalian cell, such as a *Homo sapiens* cell, the endogenous enzymes can provide for the desired biosynthetic pathway, optionally upregulating the endogenous genes or overexpressing genes encoding one or more of the native enzymes from recombinantly introduced transgenes. In embodiments where the desired end-product is N-acetylserotonin, serotonin or 5HTP, endogenous genes encoding enzymes catalyzing the subsequent reaction steps in the Shikimate pathway can optionally be downregulated or knocked-out, e.g., using CRISPR-Cas9 technology or other methods known in the art.

Alternatively, one or more of the enzymes of the biosynthetic pathway may be heterologous to the recombinant host cell, introduced by recombinant techniques known in the art and described, e.g., in WO 2013/127914 A1, WO 2013/127915 A1, WO 2015/032911 A1, WO 2017/167866 A1, WO 2017/202897 A1, WO 2018/037098 A1 and WO 2018/108966 A1 (all Danmarks Tekniske Universitet) and in US 2014/134689 AA (University of California), all of which hereby incorporated by reference in their entireties. Suitable, non-limiting, sources of heterologous enzymes for introducing a biosynthetic pathway for melatonin, N-acetylserotonin, serotonin, 5HTP or other indole-derivatives are shown in Table 3 and Table 4. Typically, the host cell is transformed with transgenes encoding the heterologous enzymes under the control of a promoter suitable for the selected host cell and/or linked to elements that promote integration of the nucleic acid sequence into the host cell genome.

TABLE 3

Examples of enzyme sources for biosynthetic pathways

| Name (EC #) | Species | Genbank, RefSeq or UniProtKB accession No. |
|---|---|---|
| L-tryptophan hydroxylase (EC 1.14.16.4) (TPH) | *Oryctolagus cuniculus* TPH1 | P17290-1, v2 |
| | *Homo sapiens* TPH1 | NP_004170.1 |
| | *Homo sapiens* TPH2 | NP_775489.2 |
| | *Gallus gallus* | NP_990287.1 |
| | *Mus musculus* | NP_033440.1 |
| | *Equus caballus* | NP_001075252.1 |
| | *Schistosoma mansoni* | AAD01923.1 |
| 5HTP decarboxylase (EC 4.1.1.28) (DDC) | *Acidobacterium capsulatum* | WP_015898075.1 |
| | *Rattus norwegicus* | XP_006251536.1 |
| | *Sus scrofa* | NP_999019.1 |
| | *Homo sapiens* | P20711-1, v2 |
| | *Capsicum annuum* | NP_001312016.1 |
| | *Drosophila caribiana* | AAM80956.1 |
| | *Maricaulis maris* (strain MCS10) | ABI65701.1 |
| | *Oryza sativa* subsp. *Japonica* | XP_015648768.1 |
| | *Pseudomonas putida* S16 | WP_013972057.1 |
| | *Catharanthus roseus* | P17770-1, v1 |
| | *Candidatus Koribacter versatilis* Ellin345 | ABF41161.1 |

TABLE 3-continued

Examples of enzyme sources for biosynthetic pathways

| Name (EC #) | Species | Genbank, RefSeq or UniProtKB accession No. |
| --- | --- | --- |
| | *Draconibacterium orientale* | AHW60462.1 |
| | *Verrucosispora maris* | WP_013735011.1 |
| serotonin | *Streptomyces griseofuscus* | AHL44344.1/W8QGX9 |
| acetyltransferase | *Chlamydomonas reinhardtii* | BAH10512.1 |
| (EC 2.3.1.87 or 2.3.1.5) | *Bos Taurus*, optionally with A55P mutation | DAA18183.1 |
| (AANAT) | *Gallus gallus* | NP_990489.1 |
| | *Homo sapiens* | NP_001079.1 |
| | *Mus musculus* | XP_011246971.1 |
| | *Oryctolagus cuniculus* | XP_008249128.1 |
| | *Ovis aries* | NP_001009461.1 |
| acetylserotonin | *Homo sapiens* | P46597-1, v1 |
| O-methyltransferase | *Ocimum basilicum* | Q9XGV9-1, v1 |
| (EC 2.1.1.4) | *Bos taurus* | P10950-1, v2 |
| (ASMT) | *Takifugu rubripes* | XP_011609423.1 |
| | *Macaca mulatta* | NP_001028112.1 |
| | *Elephantulus edwardii* | XP_006902482.1 |
| | *Oryza sativa* | XP_015610997.1 |
| | *Rattus norvegicus* | NP_653360.2 |
| | *Gallus gallus* | NP_990674.1 |
| | *Chromobacterium violaceum* | WP_011135808.1 |
| | *Desulfotomaculum kuznetsovii* DSM 6115 | YP_004515712.1 |
| | *Xenopus (Silurana) tropicalis* | NP_001011409.1 |
| | *Pseudomonas fluorescens* | WP_019095725.1 |
| | *Candidatus Solibacter usitatus* | WP_011682595.1 |
| | *Fenneropenaeus chinensis* | AAZ66373.1 |
| | *Arabidopsis thaliana* | NP_200227.1 |
| pterin-4-alpha-carbinolamine | *Pseudomonas aeruginosa* | WP_003085898.1 |
| dehydratase | *Bacillus cereus* var. *anthracis* | WP_000979542.1 |
| (EC 4.2.1.96) | *Corynebacterium glutamicum* ATCC 14067 | WP_003860504.1 |
| (PCBD1) | *Lactobacillus ruminis* ATCC 25644 | WP_003692157.1 |
| | *Rhodobacteraceae bacterium* HTCC2083 | WP_009831434.1 |
| | *Homo sapiens* | NP_000272.1 |
| | *Chromobacterium violaceum* | WP_011135913 |

Other biosynthetic pathways for the production of, e.g., serotonin or melatonin can also be used. For example, in one aspect, the recombinant cell additionally or alternatively comprises a biosynthetic pathway for producing serotonin from L-tryptophan via a tryptamine intermediate. Park et al. (Appl Microbiol Biotechnol 2011; 89(5):1387-1394) describes the production of serotonin in *E. coli* by dual expression of a tryptophan decarboxylase (TDC) and tryptamine 5-hydroxylase (T5H), with TDC decarboxylating tryptophan into tryptamine, after which T5H hydroxylates tryptamine into serotonin. Adding an AANAT and an ASMT to the biosynthetic may then provide for the production of N-acetylserotonin and melatonin. Suitable TDCs and T5Hs include those endogenous to plants, such as tomato or *Oryza sativa* subsp. *japonica* (Rice), UniProtKB—Q6ZJK7 (TDC1 ORYSJ) and UniProtKB—Q2QUC5 (C71P1 ORYSJ), respectively.

Preferably, the biosynthetic pathway comprises one or more enzymes shown in Table 4. In some embodiments, the biosynthetic pathway is for producing 5HTP, and comprises a TPH enzyme described in WO 2017/167866 A1, preferably SEQ ID NO:13 of WO 2017/167866 A1 with E2K, N97I and P99C mutations introduced. In some embodiments, the biosynthetic pathway is for producing serotonin, and further comprises a DDC, e.g. *Candidatus Koribacter versatilis* Ellin345 (ABF41161.1). In some embodiments, the biosynthetic pathway is for producing N-acetylserotonin, and further comprises an AANAT described in WO 2018/108966 A1, preferably *Streptomyces griseus* AANAT (WP_011135913) with a D63G mutation. In some embodiments, the biosynthetic pathway is for producing melatonin, and further comprises an ASMT described in WO 2017/202897 A1, e.g., *Homo sapiens* ASMT (P46597.1) comprising an A258E, G260D or T272A mutation, such as an A258E mutation and, optionally, a V305A mutation.

As described herein, YhjV can provide for import and export of indole-derivatives via antiport transporter activity. For example, YhjV provides for export of melatonin and for import of L-tryptophan, and for export of 5HTP and for import of L-tryptophan. This can be particularly advantageous in embodiments where a first indole-derivative is the substrate for a biosynthetic pathway where a second indole-derivative is the product of interest. In such cases, each molecule of imported substrate may be coupled with the export of one molecule of exported product, thereby avoiding undue intracellular accumulation of either substrate or product. So, in a particular aspect, the recombinant cell is genetically modified to overexpress a gene encoding YhjV (SEQ ID NO:2), or a functionally active variant and/or fragment thereof, and is capable of producing a second indole-derivative from a first indole-derivative via the biosynthetic pathway. The first and second indole-derivatives can be chosen from any substrate/product indole-derivatives pair for which a biosynthetic pathway is known in the art. In the Shikimate pathway, any compound can serve as the first or the second indole-derivative. In some embodiments, the first indole-derivative is L-tryptophan. In some embodiments, the first indole-derivative is tryptamine. In some embodiments, the first indole-derivative is serotonin. In some embodiments, the first indole-derivative is N-acetylserotonin. In some embodiments, the first indole-derivative is melatonin. In some embodiments, the second indole-derivative is selected from melatonin, N-acetylserotonin, serotonin, 5HTP and tryptamine. In a particular embodiment, the second indole-derivative is melatonin. In specific embodiments, the first and second indole-derivatives are (a) tryptophan and melatonin, respectively; (b) tryptophan and N-acetylserotonin, respectively; (c) tryptophan and serotonin, respectively; and (d) tryptophan and 5-hydroxytryptophan, respectively. In other specific embodiments, the second and first indole-derivatives are (a) tryptophan and melatonin, respectively; (b) tryptophan and N-acetylserotonin, respectively; (c) tryptophan and serotonin, respectively; and (d) tryptophan and 5-hydroxytryptophan, respectively.

Other indole-derivatives of interest, typically as a second indole-derivative, include Almotriptan, Alosetron, Bopindolol, Bromocriptine, Cabergoline, Carprofen, Carvedilol, Ceruletide, Delavirdine, Deserpidine, Dihydroergotamine, Dihydroergotoxine, Dolasetron, Eletriptan, Ergoloid mesylate, Ergonovine, Ergotamine, Etodolac, Fluvastatin, Frovatriptan, Gonadorelin, Goserelin, Indomethacin, Lisuride, Methylergonovine, Methysergide, Nafarelin, Naratriptan, Nicergoline, Octreotide, Ondansetron, Pentagastrin, Pergolide, Pindolol, Rescinnamine, Reserpine, Rizatriptan, Sertindole, Sumatriptan, Tadalafil, Vapreotide, Vilazodone, Vinblastine, Vincristine, Vindesine, Vinorelbine, Voacamine, Yohimbine, Zafirlukast, Zolmitriptan, (5-hydroxyindol-3-yl)acetaldehyde, 5,6-dihydroxyindole-2-carboxylate, 5-Hydroxyindoleacetate, 5-Methoxyindoleacetate, 6-Hydroxymelatonin, indol-3-ylacetaldehyde, indole-3-acetate, N-Methylserotonin and tryptaminium.

Host Cell

The recombinant cell (host cell) is preferably tryptophan autotrophic (i.e., capable of endogenous biosynthesis of L-tryptophan), grows on synthetic medium with suitable carbon sources, and expresses a suitable RNA polymerase (such as, e.g., T7 polymerase). In all known microorganisms, tryptophan production takes place via a single metabolic pathway (Somerville, R. L., Herrmann, R. M., 1983, Amino acids, Biosynthesis and Genetic Regulation, Addison-Wesley Publishing Company, U.S.A.: 301-322 and 351-378; Aida et al., 1986, Biotechnology of amino acid production, progress in industrial microbiology, Vol. 24, Elsevier Science Publishers, Amsterdam: 188-206). Tryptophan precursor can also be provided exogenously to the host cell, e.g., by adding L-tryptophan to the medium of a recombinant host cell. In some embodiments, particularly suitable for host cells of the family Enterobacteriaceae, such as E. coli, the host cell expresses E. coli TrpE (Anthranilate synthase component 1; Uniprot P00895) or a S40F mutant thereof (Caligiuri et al., Science 1991; 252(5014):1845-8; Caligiuri et al., J Biol Chem 1991; 266(13):8328-35), known to promote the first step of the subpathway that synthesizes L-tryptophan from chorismate.

The recombinant host cell is also typically capable of biosynthesizing and/or regenerating the cofactors used by the enzymes in the biosynthetic pathway. In particular, the recombinant host cell is preferably capable of biosynthesizing, regenerating, or bio-synthesizing and regenerating, one or more cofactors for TPH, AANAT and ASMT (FIG. 1).

To provide cofactor for TPH-catalyzed hydroxylation of tryptophan, the recombinant host cell is preferably capable of biosynthesizing one or both of THB and MH4 via endogenous or heterologous (introduced) pathways. For example, endogenous pathways for THB biosynthesis are present in mammalian cells. Microbial cells generally do not biosynthesize THB endogenously, but it has been reported that the endogenous compound MH4 may substitute for or replace THB as cofactor for TPH in such cells (US 2014/134689 AA; University of California). GTP cyclohydrolase I (such as, e.g. FolE)-catalyzed pterin biosynthesis resulting in MH4 takes place in many organisms including both prokaryotes and eukaryotes (see, e.g. FIG. 9 of US 2014/134689 AA). So, for example, in one embodiment, the microbial host cell is an E. coli cell, and comprises the endogenous enzymes FolE, FolX, P-ase, and FolM (Uniprot POAFS3), optionally upregulated or expressed from a transgene on one or more introduced vectors. Preferably, at least FolM is overexpressed. Further, useful FolE variants such as, e.g., FolE (T1981) are described in, e.g., WO 2017/167866. Orthologs of these enzymes in other microbial host cells, e.g., of the family Enterobacteriaceae can also be identified and upregulated or overexpressed.

Alternatively, enzymes of biosynthetic pathways for producing and/or regenerating THB can be introduced recombinantly, as described in, e.g. WO 2013/127914 A1, WO 2013/127915 A1 and WO 2015/032911 A1 (Danmarks Tekniske Universitet) and in US 2014/134689 AA (University of California). Briefly, in one embodiment, the recombinant cell comprises an exogenous pathway producing THB from GTP and herein referred to as "first THB pathway", comprising a GTP cyclohydrolase I (GCH1), a 6-pyruvoyl-tetrahydropterin synthase (PTPS), and a sepiapterin reductase (SPR). The addition of such a pathway to microbial cells such as E. coli (3M101 strain), S. cerevisiae (KA31 strain) and Bacillus subtilis (1A1 strain (TrpC2)) has also been described in, e.g., U.S. Pat. No. 7,807,421. In one embodiment, the recombinant cell comprises a pathway producing THB by regenerating THB from HTHB, herein referred to as "second THB pathway", comprising a 4a-hydroxytetrahydrobiopterin dehydratase (PCBD1) and, optionally, a 6-pyruvoyl-tetrahydropterin synthase (DHPR). The second THB pathway can convert the HTHB formed by the L-tryptophan hydroxylase-catalyzed hydroxylation of L-tryptophan back to THB, thus allowing for a more cost-efficient 5HTP synthesis. Preferably, at least microbial host cells, such as host cells of the family Enterobacteriaceae, e.g., E. coli, may be transformed with a heterologous gene expressing a PCBD1, such as a PCBD1 shown in Table 3, e.g., Chromobacterium violaceum PCBD1 (WP 011135913).

Most types of host cells (e.g., mammalian host cells, yeast host cells such as S. cerevisiae, bacteria such as E. coli, etc.) are capable of producing and regenerating acetyl-CoA (AcCoA) and SAM; the cofactors for AANAT and ASMT, respectively. AcCoA serves as a metabolic cofactor in the AANAT reaction, but is also part of other, endogenous pathways in, e.g., microbial cells. SAM is a principal methyl donor in various intracellular transmethylation reactions. It is synthesized in the cell through SAM synthetase from methionine and ATP, and natively generated through the SAM cycle, which consists of a methyl transferase, an S-adenosyl-L-homocysteine hydrolase, a folate transferase, and an S-adenosyl-methionine synthetase (Lee et al., Korean J. Chem. Eng. 2010, 27, 587-589). Accordingly, in the ASMT-catalyzed, last reaction in the production of melatonin from L-tryptophan, N-acetylserotonin and SAM are converted to melatonin and SAH. SAH can then be recycled back to SAM via the SAM-cycle in microbial cells where the S-adenosyl-L-methionine cycle is native (or exogenously added) and constitutively expressed, such as, e.g., in E. coli. The enzymes of such native pathways can also, in needed, be upregulated or expressed from an exogenously introduced vector, using well-known recombinant techniques known in text books referenced elsewhere herein. Non-limiting and exemplary nucleic acids encoding enzymes of the SAM cycle for use in aspects and embodiments of the present invention include those shown in Table 1 of WO 2015/032911 A1, which is hereby specifically incorporated by reference.

Process

In one aspect, the invention also provides for a process of preparing the recombinant host cell. Typically, the process comprises introducing into the host cell, typically via transformation, one or more vectors comprising transgenes encoding the desired integral membrane protein and, optionally, enzymes providing for the biosynthetic pathway, using standard methods known in the art and cited elsewhere herein. The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizen, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278). As described above, the vector, once introduced, may be maintained as a chromosomal integrant or as a self-replicating extra-chromosomal vector.

Preferably, for transformation of an *E. coli* or other bacterial host cell, the vectors are designed as follows: A Ptrc promoter is used to control the expressions of a gene or an artificial operon containing up to three genes connected with a linker sequence, in order to express the genes at a suitable level so that the introduction of heterologous genes/pathways do not overdraw substrates or energy in the host cell. In one particular embodiment, the recombinant microbial cell, preferably derived from a bacterial cell, is transformed according to a strategy outlined in the Examples.

Preferably, for transformation of a yeast host cell such as *S. cerevisiae*, the heterologous genes are integrated onto chromosome using a homologous recombination based method (Mikkelsen et al., 2012). As compared with gene expression based on plasmids, the chromosomally integrated genes can be expressed with higher fidelity and resulted in better protein translation, in particular for multiple gene co-expression systems.

The transformation can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product, including those referred to above and relating to measurement of 5HTP production. Expression levels can further be optimized to obtain sufficient expression using methods well known in the art and as disclosed herein.

In a preferred embodiment, the host cell is a microbial cell. The microbial host cell for use in the present invention is typically unicellular and can be, for example, a bacterial cell, a yeast host cell, a filamentous fungal cell, an algeal cell, or a mammalian cell.

In one embodiment, the host cell is bacterial cell, e.g., of the family Enterobacteriaceae; a *Bacillus* cell such as a *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, or a *Bacillus thuringiensis* cell; or a *Streptomyces* cell such as a *Streptomyces lividans* or *Streptomyces murinus* or *Strepromyces coelicolor* cell. In a particular embodiment, the recombinant microbial cell is derived from cell of the *Escherichia* genus, such as an *Escherichia coli* cell. In another particular embodiment, the host cell is of an *E. coli* strain selected from the group consisting of K12.DH1 (Proc. Natl. Acad. Sci. USA, volume 60, 160 (1968)), JM101, JM103 (Nucleic Acids Research (1981), 9, 309), JA221 (J. Mol. Biol. (1978), 120, 517), HB101 (J. Mol. Biol. (1969), 41, 459) and C600 (Genetics, (1954), 39, 440) and BL21.

In one embodiment, the host cell is a fungal cell, such as, e.g., a yeast cell. Exemplary yeast cells include *Candida*, *Hansenula*, *Kluyveromyces*, *Pichia*, *Saccharomyces*, *Schizosaccharomyces* and *Yarrowia* cells. In a particular embodiment, the host cell is an *S. cerevisiae* cell. In another particular embodiment, the host cell is of an *S. cerevisie* strain selected from the group consisting of *S. cerevisiae* KA31, AH22, AH22R-, NA87-11A, DKD-5D and 20B-12, *S. pombe* NCYC1913 and NCYC2036 and *Pichia pastoris* KM71.

In one embodiment, the host cell is a mammalian cell. Examples of mammalian cells include, but are not limited to, CHO, CHO-S, HEK, HEK293, HEK-293F, Expi293F, PER.C6, NS0 cells, Sp2/0 cells and lymphocytic cells.

For example, for overexpression of YhjV, or a fragment or variant thereof, the following strategies are contemplated: In an *E. coli* host cell, the native YhjV expression level may be enhanced by, for example, exchanging the promoter or 5'-UTR sequences. Alternatively, in an *E. coli* host cell, additional YhjV gene copies, or transgenes encoding a fragment or variant of YhjV, may be inserted in the genome or introduced via plasmids, e.g., low-copy plasmids, and the additional gene expression driven by a promoter. In other microbial cells, such as yeast cells, or mammalian cells, a transgene encoding YhjV or the fragment or derivative thereof may be introduced via a plasmid and/or into the genome.

In another aspect, the invention provides for compositions comprising a recombinant cell according to any aspect or embodiment described herein in a medium comprising at least 2 g/L melatonin, such as at least 2.5 g/L melatonin, such as at least 3 g/L, such as at least 4 g/L, such as at least 5 g/L, such as at least 10 g/L. In a particular embodiment, the recombinant cell is of the family Enterobacteriaceae, such as, e.g., an *E. coli* cell.

The preparation of recombinant cells capable of producing indole-derivatives such as, e.g., melatonin has been extensively described elsewhere, see, e.g., WO 2013/127915 A1, WO 2015/032911 A1, WO 2017/167866 A1, WO 2017/202897 A1 and WO 2018/037098 A1 (Danmarks Tekniske Universitet). Suitable methods and plasmids for transformation of bacterial cells, such as e.g. *E. coli* cells, with enzymes of a melatonin-production pathway are described in Example 1 and Table 5, respectively. Based on the information provided, a person of skill in the art would be able to prepare other types of host cells, e.g., yeast or mammalian cells, comprising the relevant biosynthetic pathway.

Methods

In some aspects, the invention provides for a method for producing an indole-derivative using the recombinant cells of any aspect or embodiment described herein. Preferably, the indole-derivative is selected from melatonin, N-acetylserotonin, serotonin and 5HTP. Typically, the method comprises culturing the recombinant cell in a culture medium comprising a carbon source. Suitable fermentation methods include batch (batch culture), fed batch (feed), repeated fed batch (repetitive feed) and continuous process. In one embodiment, the method is a fed-batch fermentation process, optionally according to the one described in Example 1. In some embodiments, the medium further comprises tryptophan. The desired compound can then optionally be isolated or retrieved from the medium, and optionally further purified. Also provided is a method of preparing a composition comprising such an indole-derivative, further comprising adding one or more suitable excipients to obtain the composition.

Suitable carbon sources include carbohydrates such as monosaccharides, oligosaccharides and polysaccharides, such as, e.g., glucose, fructose, sucrose, xylose, mannose, galactose, rhamnose, arabinose, fatty acids, glycerine, glycerol, acetate, pyruvate, gluconate, starch, glycogen, amylopectin, amylose, cellulose, cellulose acetate, cellulose nitrate, hemicellulose, xylan, glucuronoxylan, arabinoxylan, glucomannan, xyloglucan, lignin, and lignocellulose. Other polymers or monomers may also be used.

The culture conditions are adapted to the recombinant cell, and can be optimized to maximize production of the indole-derivative by varying culture conditions and media components as is well-known in the art. In one embodiment, no L-tryptophan is added to the medium, instead relying on L-tryptophan precursor biosynthesized by the recombinant cell. In one embodiment, L-tryptophan is added to the medium.

For a recombinant *Escherichia coli* cell, exemplary media include LB medium and M9 medium (Miller, Journal of Experiments in Molecular Genetics, 431-433, Cold Spring Harbor Laboratory, New York, 1972), optionally supplemented with one or more amino acids. When an inducible promoter is used, the inductor can also be added to the medium. Examples include the lac promoter, which can be activated by adding isopropyl-beta-thiogalacto-pyranoside (IPTG) and the GAL/BAD promoter, in which case galactose/arabinose can be added. The culturing can be carried out a temperature of about 10 to 40° C. for about 3 to 72 hours, if desired, with aeration or stirring.

For a recombinant yeast cell, Burkholder minimum medium (Bostian, K. L., et al. Proc. Natl. Acad. Sci. USA, volume 77, 4505 (1980)), SD medium containing 0.5% of Casamino acid (Bitter, G. A., et al., Proc. Natl. Acad. Sci. USA, volume 81, 5330 (1984), and Delft medium (Verduyn et al., Yeast 1992, 8, 501-517) can be used. The pH is preferably adjusted to about 5-8.

Isolation of the desired product from the cell culture can be achieved, e.g., by separating the compound from the cells using a membrane, using, for example, centrifugation or filtration methods. The product-containing supernatant is then collected. Further purification of the desired compound can then be carried out using known methods, such as, e.g., salting out and solvent precipitation; molecular-weight-based separation methods such as dialysis, ultrafiltration, and gel filtration; charge-based separation methods such as ion-exchange chromatography; and methods based on differences in hydrophobicity, such as reversed-phase HPLC; and the like. In one embodiment, ion-exchange chromatography is used for purification of serotonin. In one embodiment, reverse-phase chromatography is used for separation and/or purification of melatonin. An exemplary method for purification of these indolamines using reversed-phase chromatography is described in Harumi et al., (1996) (J Chromatogr B 675:152-156).

Once a sufficiently pure preparation has been achieved, suitable excipients, stabilizers can optionally be added and the resulting preparation incorporated in a composition for use in preparing a product such as, e.g., a dietary supplement, a pharmaceutical, a cosmeceutical, or a nutraceutical. For a dietary supplement comprising melatonin, each serving can contain, e.g., from about 0.01 mg to about 100 mg melatonin, such as from about 0.1 mg to about 10 mg, or about 1-5 mg, such as 2-3 mg. Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

The invention is illustrated by the following Examples, which are not to be construed as limiting.

Example 1

This Example describes testing *E. coli* cells for melatonin tolerance, the identification of melatonin transporters in *E. coli*, as well as the effects of overexpressing the transporters on melatonin production.

Materials and Methods

Screening using Growth Profiler

The *E. coli* Keio strains (single gene deleted strains) were inoculated into 400 µl of M9+0.2% glucose media supplemented with kanamycin (50 µg/ml) in 96 deep well-plate picking the single colonies in LB-agar plates. Then, the plate was incubated at 30° C. with 300 rpm overnight (incubated for 18-24 h). The wild type strain *E. coli* BW25113 was used as a control. The following day, the saturated pre-cultures were diluted 100 fold into 300 µl of M9+0.2% glucose media (and antibiotics as required) supplemented with 4.4% of ethanol or 4.4% of ethanol and 4.4 g/L of melatonin so that the resulting final concentration would be 4% of ethanol and 4 g/L of melatonin in 96 well MTP plate. In case of the RBS library of yhjV, screening was performed at 5 g/L of melatonin instead of 4 g/L. Then, the culture plates were incubated in Growth Profiler (Enzyscreen, Heemstede, Netherland) at 30° C. and 250 RPM for 48 h with constant monitoring of the growth by taking picture in every 20 minutes interval. Using the GP software (GP960Viewer version 1.0.0.4, Enzyscreen, Heemstede, Netherland), the pictures data was converted into digital OD600 nm values and the growth curves were compared.

Preparation of Strains

Melatonin production strains were derived from BW25113. Heterologous genes introducing 5HTP decarboxylase (DDC); aralkylamine N-acetyltransferase (AANAT); tryptophan hydroxylase (TPH); a pterin-4-alpha-carbinolamine dehydratase (PCBD1), and acetylserotonin O-methyltransferase (ASMT) enzymatic activities were overexpressed using constitutive promoters. In some strains, *E. coli* FolM (POAFS3) and a mutant of *E. coli* TrpE (540F; Caligiuri et al., Science 1991; 252(5014):1845-8; Caligiuri et al., J Biol Chem 1991; 266(13):8328-35) were also overexpressed. The details of the enzymes used to construct the melatonin biosynthetic pathway are described in Table 4. The details of the strains used in this Example are listed in Table 5. The sequences of promoters used for expressing the enzymes are listed Table 6.

TABLE 4

Enzymes

| Activity | Source (Genbank or UniProtKB accession No.) | Reference |
|---|---|---|
| TPH | Residues M1 and E147 to T460 of Homo sapiens TPH2 (NP_775489.2); E2K, N97I and P99C substitutions | WO 2017/167866 A1 |
| DDC | Candidatus Koribacter versatilis Ellin345 (ABF41161.1) | |
| PCBD1 | Chromobacterium violaceum PCBD1 (WP_011135913) | |
| AANAT | Streptomyces griseus AANAT (WP_011135913), D63G | WO 2018/108966 A1 |
| ASMT | Homo sapiens ASMT (P46597.1), A258E, V305A | WO 2017/202897 A1 |

TABLE 5

Melatonin production strain list

| Strains | Overexpression | Other information* |
|---|---|---|
| HMP2360 | Ptrc_ddc, Ptrc_aanat J23107_tph_pcbd1_asmt | ΔTnaA ΔTrpR FolE(T198I) ΔPfolE::PJ23100 |
| HMP2993 | P2_ddc; J23101_aanat | ΔTnaA ΔTrpR FolE(T198I) ΔPfolE::PJ23100 ΔFhuA |
| HMP2818 | P2_ddc; J23101_aanat J23107_tph_pcbd1_asmt | ΔTnaA ΔTrpR FolE(T198I) ΔPfolE::PJ23100 ΔFhuA |
| HMP3337 | P2_ddc; J23101_aanat J23107_tph_pcbd1_asmt J23107_yhjV | ΔTnaA ΔTrpR FolE(T198I) ΔPfolE::PJ23100 ΔFhuA |
| HMP3333 | P2_ddc; J23101_aanat J23107_tph_pcbd1_asmt J23107_garP(R135*) | ΔTnaA ΔTrpR FolE(T198I) ΔPfolE::PJ23100 ΔFhuA |
| HMP3335 | P2_ddc; J23101_aanat J23107_tph_pcbd1_asmt J23107_acrAB | ΔTnaA ΔTrpR FolE(T198I) ΔPfolE::PJ23100 ΔFhuA |
| HMP3339 | P2_ddc; J23101_aanat J23107_tph_pcbd1_asmt J23107_argO | ΔTnaA ΔTrpR FolE(T198I) ΔPfolE::PJ23100 ΔFhuA |
| HMP2820 | P2_ddc; J23101_aanat J23107_tph_pcbd1_asmt | ΔTnaA ΔTrpR FolE(T198I) ΔPfolE::PJ23100 ΔFhuA PJ23107-folM |
| HMP3355 | P2_ddc; J23101_aanat J23107_tph_pcbd1_asmt J23107_yhjV | ΔTnaA ΔTrpR FolE(T198I) ΔPfolE::PJ23100 ΔFhuA PJ23107-folM |
| HMP3427 | P2_ddc; J23101_aanat J23107_tph_pcbd1_asmt | ΔTnaA ΔTrpR FolE(T198I) ΔPfolE::PJ23100 ΔFhuA TrpE(S40F) |
| HMP3428 | P2_ddc; J23101_aanat J23107_tph_pcbd1_asmt J23107_yhjV | ΔTnaA ΔTrpR FolE(T198I) ΔPfolE::PJ23100 ΔFhuA TrpE(S40F) |
| HMP3403 | J23107_tph_pcbd1 | ΔTnaA ΔTrpR FolE(T198I) PfolE::PJ23100 ΔgstA ΔFhuA |
| HMP3404 | J23107_tph_pcbd1 J23107_yhjV | ΔTnaA ΔTrpR FolE(T198I) PfolE::PJ23100 ΔgstA ΔFhuA |
| pHM345 (plasmid) | J23107_tph_pcbd1_asmt | |
| pHM635 (plasmid) | J23107_yhjV | |

*"PfolE::PJ23100" indicates that the native promoter of the folE gene has been replaced by J23100.

TABLE 6

Promoter sequences used

| Promoter | Sequence | SEQ ID NO: |
|---|---|---|
| Ptrc | AACTGTTAATTAGTAGGCCGAGCATATTAC | 13 |
| P2 | AAAAAGAGTATTGACTTCGCATCTTTTTGTACCTATAATGTGTGGA | 14 |
| J23101 | TTTACAGCTAGCTCAGTCCTAGGTATTATGCTAGC | 15 |
| J23107 | TTTACGGCTAGCTCAGCCCTAGGTATTATGCTAGC | 16 |
| J23100 | TTGACGGCTAGCTCAGTCCTAGGTACAGTGCTAGC | 17 |

Small-Scale Production Assay

To measure the production of melatonin, bacterial cells were cultivated in deep-well plates in glucose slow release (GSR) medium mimicking fed-batch fermentation at 30° C. 1 L of GSR medium contains 15 g of Maltodextrin (dextrose equivalent 4.0-7.0, Sigma Aldrich 419672), 200U of Amyloglucosidase (Sigma Aldrich 10115, 70 U/mg) for glucose release, 40 g of MES monohydrate (Sigma Aldrich), 1.2 g of K2HPO4, 7 g of Ammonium sulfate, 120 mg of Sodium citrate, 8 mg of $ZnCl_2$, 12 mg of $FeSO_4·7H_2O$, 9 uM of $CaCl_2$, 12.5 mM of $MgSO_4·7H_2O$, as well as trace elements and vitamins. The media pH was adjusted to 6.4. The medium was supplemented with 500 mg/L tryptophan, 50 mg/L kanamycin and 100 mg/L ampicillin. The bacterial cells were cultivated at 30° C. in M9 medium for 24 hours. The precultures were diluted 100 times into GSR medium and cultured at 30° C. After 24 hours, the supernatant was collected by filtering the broth with 0.2 μm filters (Pall, New York, USA). The concentration of melatonin in the supernatant was determined by HPLC.

Fed-Batch Fermentation

Fed-batch fermentation was carried out using ambr250 reactors (Sartorius, Goettingen, Germany). The cryo stocks of strains were transferred into 50 ml of M9 media with 0.2% glucose and required antibiotics. The flasks were incubated at 250 RPM and 37° C. overnight. Two millilitres of saturated overnight cultures were inoculated into 100 ml of M9 media with 0.2% glucose and required antibiotics in 250 ml single-use bioreactors (ambr250, Sartorius, Germany).

The cultivations were performed at 30° C. using the cascade of stirring and aeration to control the levels of dissolved oxygen at 40%. The level of stirring in cascade was kept between 1000 rpm and 4000 rpm, while airflow levels were kept between 100 ml/min and 250 ml/min. The pH of the cultures was maintained at 6.0, using 7% ammonium hydroxide.

After the batch phase, 36% w/v glucose solution with other M9 media components and antibiotics was fed in the reactors with strain HMP3427 and HMP3428 using the exponential feeding with specific growth rate of 0.05 $h^{-1}$. For the strains HMP3337, HMP2818, HMP3355 and HMP2820, the feed medium contained, in addition to 36% w/v glucose solution and M9 media components, 15 g/L of tryptophan and it was added using the exponential feeding profile with specific growth rate of 0.05 h-1.

The duration of the feeding phase was up to 72 h, depending on the strain used in the specific cultivation. The culture samples of 2 ml were withdrawn every 7 h to track the progress of cultivation. The biomass concentration was determined using optical density measurement at the wavelength 600 nm. The HPLC analysis was used for determination of residual medium components and metabolites concentrations. For determination of extracellular metabolites and residual sugars, 1 ml of the culture broth was centrifuged at 4000 rpm at 4 C.° for 10 min and the supernatant filtered and injected into HPLC. For determination of total metabolite concentration, 500 µl of culture broth was mixed with 500 µl of acetonitrile: isopropanol solvent mixture (ratio 1:1) and vigorously vortexed for 30 seconds and frozen at −80 C°. The frozen samples were thawed and extracted at room temperature by shaking at 2000 rpm for 30 min. Subsequently, the samples were centrifuged at 4000 rpm and 4 C.° for 10 min. The supernatant was filtered and injected into HPLC.

HPLC Analytics

The same HPLC protocol was used to separate and detect melatonin pathway intermediates and possible by-products, including melatonin, tryptophan, 5-hydroxytryptophan (5-HTP), serotonin, N-acetylserotonin, and N-acetyl-tryptamine.

N-acetyl-tryptamine was purchased from Santa Cruz Biotechnology (Dallas, Texas, US). All other compounds were purchased from Sigma Aldrich (St. Louis, Missouri, USA).

Water for all solutions was purified in a Milli-Q system (Millipore, Milford, MA, US). LC-MS grade acetic acid (Sigma Aldrich, St. Louis, Missouri, USA) and Acetonitrile (Merck KGaA, Darmstadt, Germany) was use for solutions and eluents.

A Dionex 3000 HPLC (Thermos Fisher Scientific, Waltham, Massachusetts, US) was equipped with a Zorbax Eclipse Plus C18 (4.6×100 mm, 3.5 µm) column from Agilent Technologies and a precolumn filter from Phenomonex (Torrance, CA, US). The column temperature was set at 30° C. The mobile phase consisted of a A: 0.05% (v/v) acetic acid in MilliQ water and B: acetonitrile in the following gradient program: 0 min 95% A decreasing to 38.7% A in 9.4 min. and holding for 0.6 min Then returning to initial composition after 11 min and holding for 1 min. The total run time was 12 min. The flow rate was constant at 1 ml/min and injection volume was 1 ul. Detection was done by UV at wavelength 210 nm, 240 nm, 280 nm and 300 nm and 3D UV scan.

Calibration standards were prepared by diluting stock solutions of the investigated compounds. Matrix-matched standards were used to prevent matrix effects, and were prepared by mixing standards with spent media. The concentration of the calibration standards were: 0.5, 1, 2.5, 5, 10, 25, 50, 100, 250, 500, 750, 1000, 2500, 5000 mg/L. All solutions were kept in a freezer (−18° C.) when not in use. Calibrations standards were prepared freshly every week.

Data were processed by Chromeleon 7.1.3 software (Thermos Fisher Scientific, Waltham, Massachusetts, US) and the concentration of melatonin and melatonin pathway intermediates were calculated by bracketing calibration from standard curves.

Results

Growth of E. coli in the Presence of Melatonin

In order to elucidate whether melatonin production at high titers is toxic to E. coli, we tested the growth of E. coli strain in the presence of different concentrations of melatonin. Melatonin was externally added into M9 medium supplemented with 0.2% glucose and the growth curves were monitored. As shown in FIG. 2, high concentrations of melatonin inhibited E. coli growth. Compared to the control, the biomass yield decreased ~30% at 2 g/L melatonin, and further decreased about 30% at 7 g/l melatonin.

Identification of Melatonin Transporters

To identify any melatonin-specific native transporters in E. coli, an E. coli knockout library of 430 strains was screened, testing cell growth in the presence of 4 g/L (or 5 g/L) melatonin using the Growth Profiler. In such a screen, improved growth parameters (especially higher growth rate and/or lower lag time) compared to wild-type strain can be expected in case an importer is knocked-out, whereas decreased growth parameters can be expected in case an exporter is knocked-out (FIG. 3).

From the results of the first screening round, 30 candidate transporter targets could be identified. In a second round, the growth test was repeated in triplicates. From the triplicates runs, 5 transporters responsible for melatonin export were identified—YhjV, GarP, ArgO, AcrB and LysP (Table 1). No importers were identified. Without being limited to theory, it is possible that there were too many importers for the loss of one to be noticeable in this assay.

Result of Growth Profiler Screening for 5 Target Transporter Candidates:

The growth curves of the five selected transporter candidate deletion strains (target candidate knocked-out Keio strains) were accessed after running growth profiler experiments as mentioned above. With the exception of the garP deletion strain, deletion of the transporter candidate gene did not have any effect on the growth rates when the strains were grown in M9+0.2% glucose media supplemented with 4% ethanol. However, when the strains were grown in the presence of 4 g/L of melatonin in media, the growth rate was decreased for each of the 5 strains, with the most prominent effects resulting from the acre (no growth at all), yjhV (longer lag time and reduced growth rate) and garP (longer lag time and reduced growth rate) deletions. The lysP and argO deletion strains also showed reduced growth rates but not much difference in lag time as compared to the BW25113 control strain (FIG. 4).

These results show that knocking out these genes can increase the toxicity of externally supplied melatonin to the host cells, presumably because the knockouts are less able to export melatonin taken up by the cells.

Overexpression of Melatonin Transporters to Improve Melatonin Production

In order to increase the tolerance of E. coli to melatonin, each transporter was overexpressed in a low copy number plasmid. In order to tune the expression level of each transporter, degenerate sequences in ribosome binding sites (RBS) were introduced to obtain a diversity of expression levels and subjected for selection in the presence of melatonin (FIG. 5). The 5' untranslated region (5'UTR) containing RBS sequence was tcttaatcatgcnnnggannnttaacttt (SEQ ID NO:18) and it was cloned upstream of the coding sequence of each gene. The plasmid libraries were transformed into strain HMP2993 (Table 5) together with pHM345 containing some pathway genes (Table 5) and cultured in the presence of 5 g/L melatonin.

Nine to 16 isolates were obtained for each transporter and their growth profiles and melatonin production tested. The growth profiles of strains with overexpression of the transporter genes are illustrated in FIG. 6, with YhjV as an example. Small-scale production assay (400 µl cultures) was performed to test melatonin production of the selected isolates (FIG. 6). Strains carrying GarP, AcrAB, YhjV and ArgO showed improved melatonin titers, whereas LysP did not show significant improvement with any selected RBS sequences.

Four strains containing GarP, AcrAB, YhjV, ArgO overexpression plasmids were further tested in fed-batch fermentation (250 ml culture). For each transporter gene, the RBS sequence giving rise to the highest biomass melatonin yield in FIG. 6 was selected (Table 7).

The final titers of fedbatch fermentation of each strain as well as the control are listed in Table 8. One of the transporters, YhjV, increased melatonin titers from 3.9 to 5 g/L. We further tested this transporter in 2 other background strains by re-transforming the plasmid pHM635 containing the yhjV gene. In both cases, we observed 15%-40% increases of melatonin titers. The details of melatonin production during fed-batch fermentation of YhjV overexpression in 3 different background strains are shown in FIG. 7.

TABLE 7

RBS sequences used

| Transporter | 5'UTR sequence | SEQ ID NO: |
|---|---|---|
| GarP | tcttaatcatgcgggggagtgttaactttt | 19 |
| AcrAB | tcttaatcatgcgttggaggattaactttt | 20 |
| YhjV | tcttaatcatgccggggacggttaactttt | 21 |
| ArgO | tcttaatcatgctggggagggttaactttt | 22 |

TABLE 8

Melatonin titers in fed-batch fermentation
with novel transporters implemented

| Strain | Transporter | Final titer (g/L) |
|---|---|---|
| HMP2818 | control | 3.9 |
| HMP3333 | GarP | 3.6 |
| HMP3335 | AcrAB | 3.9 |
| HMP3337 | YhjV | 5.0 |
| HMP3339 | ArgO | 2.7 |

Example 2

This Example shows that overexpression of YhjV transporter improved 5HTP production.

An *E. coli* 5HTP-production strain was generated, and the effect of the YhjV transporter on 5HTP production tested. Briefly, the plasmid providing YhjV overexpression (pHM635) was transformed into a 5HTP production strain (HMP3403), resulting in strain HMP3404. In a small-scale production assay (GSR medium supplemented with 500 mg/L tryptophan and appropriate antibiotics as described materials and methods in Example 1), the new strain overexpressing YhjV improved 5HTP titers by 15% compared to the control strain (FIG. 8).

Example 3

This Example shows that complementation of YhjV restored melatonin-tolerance of yhjV knockout strain. Briefly, we complemented yhjV knockout strain with plasmid pHM635 expressing YhjV constitutively. The growth was tested in growth profiler in M9 medium supplemented with 0.2% glucose. As shown in FIG. 9, pHM635 restored the growth of yhjV knockout strain to the same level as the wild type in the presence of 4 g/L melatonin. This confirms that YhjV is responsible for melatonin export.

Example 4

This Example describes testing the influence of YhjV on the uptake of amino acids. The growth test was performed using M9 medium supplemented with 0.2% glucose and 1 mM tryptophan, as well as appropriate antibiotics (100 mg/L ampicillin or 50 mg/L kanamycin). The growth curves were monitored with Growth Profiler (Enzyscreen, Heemstede, Netherland) at 30° C. and 250 RPM for 48 h.

We first tested how YhjV transporter affects the growth of *E. coli* tryptophan. We followed the growth curves of *E. coli* wild type BW25113 (HMP0_wt), YhjV knockout (HMP3406_YhjV KO) and YhjV overexpression (HMP3405_YhjV O. E., made by transforming pHM635 into HMP0) in M9 medium containing 0.2% glucose supplemented with 1 mM tryptophan.

We found that when growing in the presence of tryptophan, YhjV knockout led to a growth defect, resulting in a much lower biomass yield compared to the wild type (FIG. 10). These results support that YhjV is also responsible for tryptophan uptake.

Example 5

This example describes using random mutagenesis and screening to identify YhjV mutants resulting higher melatonin tolerance.

Materials and Methods
Random Mutagenesis of YhjV

To generate error-prone PCR libraries of YhjV gene, we used pHM635 as the template, and primers HP-1647 (ggcagcagcctaggttaatttta) and HP-1652 (ccggggacggttaacttt-tatg) for amplification of the YhjV coding sequence. GeneMorph II Random Mutagenesis Kit (Agilent, Santa Clara, California, United States) was used for error-prone PCR. In order to generate the plasmid libraries containing random mutagenesis library of YhjV, we performed a circular PCR using the error-prone PCR as a mega-primer and plasmid pHM635 as a template. Phusion high fidelity DNA polymerase (Thermos Fisher Scientific, Waltham, Massachusetts, US) was used for the circular PCR. The resulting PCR/plasmid library was treated with DpnI restriction enzyme (Thermo Fisher Scientific) to remove the template plasmid. Finally, the DnpI treated PCR library was diluted 5 times with water and transformed into OneShot Top10 cells (Thermo Fisher Scientific) by electroporation. To check the quality of the library, 1 µl of transformants was plated on LB+amp agar plates to estimate the library size. We also sequenced 8 random colonies and 5 of them contain 1-3 mutations. The rest of the transformants were cultivated in 50 ml liquid LB medium supplemented with ampicilin (100 µg/ml) overnight. The plasmids were prepared from this cell culture using QIAprep spin miniprep kit (Qiagen, Hilden, Germany). The plasmids were stored as the random mutagenesis library of YhjV.

Screening of Beneficial Mutants

To screen for beneficial mutants of yhiV from the random mutagenesis library, we transformed the random mutagenesis library into a background strain HMP2993 (Table 5). The transformants were selected by growing in M9+0.2% glucose medium supplemented with 4 g/L or 5 g/L melatonin, 0.2% glucose and 100 µg/ml ampicillin at 30° C. for 24 h to enrich cell population containing YhjV mutants that improve melatonin tolerance. The culture was spread on LB+ampicilin agar plates to obtain single colonies. We picked 89 colonies randomly and tested their growth again in the presence of melatonin. All 89 colonies as well as the control strain (pHM635 transformed in HMP2993) was inoculated into 400 µl of M9+0.2% glucose media supplemented with ampicilin (100 µg/ml) in 96 deep-well plate. Then, the plate was incubated at 30° C. with 300 rpm overnight (incubated for 24 h). The following day, the saturated pre-cultures were diluted 100 fold into 300 μl of M9+0.2% glucose media (and ampicillin 100 μg/ml) supplemented with 4.5 g/L melatonin in 96 well MTP plate. Note that melatonin stock solution was prepared by dissolving in 75% ethanol to 170 g/L. The culture plates were incubated in Growth Profiler (Enzyscreen, Heemstede, Netherland) at 30° C. and 250 RPM for 48 h. Using the GP software (GP960Viewer version 1.0.0.4, Enzyscreen, Heemstede, Netherland), the pictures data was converted into digital OD600 nm values.

Results

The random mutagenesis library of YhjV was generated and screened as described in materials and methods. Seven out of selected 89 colonies showed improved tolerance toward melatonin and carry mutations in yhjV gene as shown in Table 9. The growth presented by OD600 difference between 48 h and 0 h in the presence of 4.5 g/L melatonin was shown in FIG. 11A. The 7 strains carry YhjV mutations showed better growth compared to the control which is HMP2993 transformed with pHM635 containing wild-type YhjV. In order to test the melatonin production of these mutants, we transformed another plasmid pHM345 (containing pathway genes, Table 5) and performed a small-scale production assay (see Example 1 materials and methods for details). The V176M mutant (pHM679) showed increased melatonin titer after 24 h of cultivation (FIG. 11B). We conclude that the efficiency of YhjV can be further improved by mutagenesis to benefit the tolerance or production of targeted chemicals.

TABLE 9

YhjV mutations accumulated in high melatonin screening

| Plasmid ID | Mutation in YhjV protein |
|---|---|
| pHM670 | G108W |
| pHM671 | A260V |
| pHM672 | F187L |
| pHM676 | I182T |
| pHM679 | V176M |
| pHM680 | I151F |

LIST OF REFERENCES

UniProtKB—P37660 (YHJV_ECOLI)
Kell, "Control of metabolite efflux in microbial cell factories: current advances and future prospects". Available at: www.osf.io/7t8 gm/online [Accessed 1 Oct. 2018]
Sargentini et al., Mutation Research 793-794 (2016) 1-14.
EP2267145 A1 (Evonik Degussa GmbH)
WO 2013/093737 A1 (BASF)
WO 2013/127915 A1 (Danmarks Tekniske Universitet)
WO 2015/032911 A1 (Danmarks Tekniske Universitet)
WO 2017/167866 A1 (Danmarks Tekniske Universitet)
WO 2017/202897 A1 (Danmarks Tekniske Universitet)
WO 2018/037098 A1 (Danmarks Tekniske Universitet)
WO 2018/108966 A1 (Danmarks Tekniske Universitet)

The invention claimed is:

1. A recombinant bacterial cell comprising a biosynthetic pathway for producing an indole-derivative selected from melatonin, N-acetylserotonin, serotonin and 5-hydroxytryptophan (5HTP),
wherein the recombinant bacterial cell is genetically modified to overexpress a gene encoding an integral membrane protein selected from YhjV (SEQ ID NO:2), GarP (SEQ ID NO:4), ArgO (SEQ ID NO: 6), AcrAB (SEQ ID NOS: 10 and 12) and LysP (SEQ ID NO: 8), a functionally active variant and/or fragment of any thereof, or a combination of any two or more thereof, thereby facilitating the passage of the indole-derivative across the cell membrane, and
wherein the amino acid sequence of the variant has a sequence identity of at least about 85% to the amino acid sequence of the integral membrane protein and the fragment comprises at least about 90% of the amino acid sequence of the integral membrane protein.

2. The recombinant bacterial cell according to claim 1, overexpressing a gene encoding YhjV, GarP, ArgO or AcrAB, or a combination of any two or more thereof.

3. The recombinant bacterial cell according to claim 1, overexpressing a gene encoding YhjV or a functionally active variant thereof.

4. The recombinant bacterial cell according to claim 1, wherein the biosynthetic pathway comprises
(a) an L-tryptophan hydroxylase;
(b) an L-tryptophan hydroxylase and a 5HTP decarboxylase;
(c) an L-tryptophan hydroxylase, a 5HTP decarboxylase, and a serotonin acetyltransferase;
(d) an L-tryptophan hydroxylase, a 5HTP decarboxylase, a serotonin acetyltransferase and an acetylserotonin O-methyltransferase;
(e) a tryptophan decarboxylase and a tryptamine 5-hydroxylase;
(f) a tryptophan decarboxylase; a tryptamine 5-hydroxylase, and a serotonin acetyltransferase; or
(g) a tryptophan decarboxylase; a tryptamine 5-hydroxylase, a serotonin acetyltransferase and an acetylserotonin O-methyltransferase.

5. The recombinant bacterial cell according to claim 1, wherein the integral membrane protein is expressed from a transgene or from an upregulated endogenous gene.

6. The recombinant bacterial cell according to claim 1, wherein at least one of the enzymes of the biosynthetic pathway is expressed from a transgene, optionally a heterologous transgene.

7. The recombinant bacterial cell according to claim 1, which is of the family Enterobacteriaceae.

8. A method for producing an indole-derivative selected from melatonin, N-acetylserotonin, serotonin and 5HTP, comprising the step of culturing the recombinant bacterial cell according to claim 1 in a culture medium comprising a carbon source, and optionally, isolating the indole-derivative.

9. The method of claim 8, wherein the medium further comprises tryptophan.

10. The recombinant cell according to claim 1, wherein the recombinant bacterial cell is capable of producing a second indole-derivative from a first indole-derivative via a biosynthetic pathway, wherein the recombinant bacterial cell is genetically modified to overexpress a gene encoding YhjV (SEQ ID NO:2), or a functionally active variant and/or fragment thereof, and wherein the amino acid sequence of the variant has a sequence identity of at least about 85% to SEQ ID NO:2 and the fragment comprises at least about 90% of SEQ ID NO: 2, wherein the first and second indole-derivatives are selected from:
(i) tryptophan and melatonin, respectively;
(ii) tryptophan and N-acetylserotonin, respectively;
(iii) tryptophan and serotonin, respectively; and
(iv) tryptophan and 5-hydroxytryptophan, respectively.

11. The recombinant bacterial cell according to claim 10, overexpressing a gene encoding YhjV or a functionally active variant thereof.

12. The recombinant bacterial cell according to claim 10, wherein the overexpression of the gene encoding YhjV or the functionally active variant and/or fragment thereof provides for an increased production of the second indole-derivative, an increased tolerance to the second indole-derivative, or both, by the recombinant bacterial cell as compared to a non-modified control cell.

13. The recombinant bacterial cell according to claim 1, wherein the functionally active variant and/or fragment of YhjV (SEQ ID NO:2) comprises a mutation in one or more amino acid residues selected from V176, G108, I151, F187, I182, C78, A260, P385, I55, N186, S268, S75 and K402.

14. The recombinant bacterial cell according to claim 13, wherein the functionally active variant and/or fragment of YhjV comprises a V176M, G108W, A260V, F187L, I182T or I151F amino acid substitution, or a combination of two or more such amino acid substitutions.

15. The recombinant bacterial cell according to claim 7, which is an *E. coli* cell.

16. A method for producing a second indole-derivative from a first indole-derivative, comprising the step of culturing the recombinant bacterial cell of claim 10 in a culture medium comprising a carbon source and the first indole-derivative, and optionally, isolating the indole-derivative, wherein the first and second indole-derivatives are selected from:
(i) tryptophan and melatonin, respectively;
(ii) tryptophan and N-acetylserotonin, respectively;
(iii) tryptophan and serotonin, respectively; and
(iv) tryptophan and 5-hydroxytryptophan, respectively.

* * * * *

SEQUENCE LISTING

<160> NUMBER OF SEQ ID NOS: 22

<210> SEQ ID NO 1
<211> LENGTH: 1272
<212> TYPE: DNA
<213> ORGANISM: Escherichia coli

<400> SEQUENCE: 1

```
atgcagcaca acacactatc gaaacacaat cagaaattgc cgtttacacg ctacgacttc      60
ggctgggttt tattatgcat aggcatggcg attggtgccg gaaccgtgct gatgccagta     120
caaattggct tgaagggaat ttgggtattt attaccgcag cgatcattgc ttatcctgcc     180
acctgggtag tgcaggacat ttatttaaaa acccttctg aaagcgattc ctgtaatgac      240
tacaccgata ttatcagtca ttacctgggg aagaactggg gaattttcct cggggttatc     300
tactttttga tgattatcca cgggattttt atctactctc tctccgtggt tttcgacagc     360
gcctcgtacc tgaaaacctt cggtttaacc gatgccgatc tttcacaatc tctactttat     420
aaagtcgcta ttttcgccgt actggtggcg attgcgtctg gtggtgaacg attactgttt     480
aagatttccg ggccaatggt ggtggtcaaa gtagggatta ttgtcgtgtt cggttttgcg     540
atgatcccgc actggaattt cgccaatata accgccttcc cgcaagcctc cgtcttttc      600 cgcgatgtct tgcttaccat tccattttgc ttcttttctg cagtatttat tcaggtactt     660
aacccaatga atattgccta tcgtaaacgg gaagcggata aagtactggc aacccggctc     720
gcgctgcgta cccaccgaat tagttatatc acgctcatcg cggtgatcct gttttttgcc     780
ttttcgttta ccttctcaat tagccacgaa gaagccgttt ctgcctttga acaaaatatc     840
tcagcactgg cgctggccgc gcaggtgatc cctgggcata tcattcatat cacctctacg     900
gtgcttaata tctttgccgt actgaccgca ttctttggca tttatctcgg tttccacgag     960
```

```
gccattaaag gcattattct caatctgtta agccgaatta ttgataccaa gaaaattaac    1020
tcacgcgtgc tgactctggc gatctgcgct tttatcgtca ttacgttgac gatttgggtt    1080
tcgtttcgtg tatcggtgct ggtgttcttt cagttgggaa gcccgttata tggtattgtg    1140
tcgtgcctca ttccgttttt cctgatctat aaagtcgcac aactggaaaa acttcgcgga    1200
tttaaagcct ggctgattct gctgtacggc attttgctat gcttgtcgcc actgttgaag    1260
ctgattgagt aa                                                        1272
```

<210> SEQ ID NO 2
<211> LENGTH: 423
<212> TYPE: PRT
<213> ORGANISM: Escherichia coli

<400> SEQUENCE: 2

```
Met Gln His Asn Thr Leu Ser Lys His Asn Gln Lys Leu Pro Phe Thr
1               5                   10                  15

Arg Tyr Asp Phe Gly Trp Val Leu Leu Cys Ile Gly Met Ala Ile Gly
            20                  25                  30

Ala Gly Thr Val Leu Met Pro Val Gln Ile Gly Leu Lys Gly Ile Trp
        35                  40                  45

Val Phe Ile Thr Ala Ala Ile Ile Ala Tyr Pro Ala Thr Trp Val Val
    50                  55                  60

Gln Asp Ile Tyr Leu Lys Thr Leu Ser Glu Ser Asp Ser Cys Asn Asp
65                  70                  75                  80

Tyr Thr Asp Ile Ile Ser His Tyr Leu Gly Lys Asn Trp Gly Ile Phe
                85                  90                  95

Leu Gly Val Ile Tyr Phe Leu Met Ile Ile His Gly Ile Phe Ile Tyr
            100                 105                 110

Ser Leu Ser Val Val Phe Asp Ser Ala Ser Tyr Leu Lys Thr Phe Gly
        115                 120                 125

Leu Thr Asp Ala Asp Leu Ser Gln Ser Leu Leu Tyr Lys Val Ala Ile
    130                 135                 140

Phe Ala Val Leu Val Ala Ile Ala Ser Gly Gly Glu Arg Leu Leu Phe
145                 150                 155                 160

Lys Ile Ser Gly Pro Met Val Val Lys Val Gly Ile Ile Val Val
                165                 170                 175

Phe Gly Phe Ala Met Ile Pro His Trp Asn Phe Ala Asn Ile Thr Ala
            180                 185                 190

Phe Pro Gln Ala Ser Val Phe Phe Arg Asp Val Leu Leu Thr Ile Pro
        195                 200                 205

Phe Cys Phe Phe Ser Ala Val Phe Ile Gln Val Leu Asn Pro Met Asn
    210                 215                 220

Ile Ala Tyr Arg Lys Arg Glu Ala Asp Lys Val Leu Ala Thr Arg Leu
225                 230                 235                 240

Ala Leu Arg Thr His Arg Ile Ser Tyr Ile Thr Leu Ile Ala Val Ile
                245                 250                 255

Leu Phe Phe Ala Phe Ser Phe Thr Phe Ser Ile Ser His Glu Glu Ala
            260                 265                 270

Val Ser Ala Phe Glu Gln Asn Ile Ser Ala Leu Ala Leu Ala Ala Gln
        275                 280                 285

Val Ile Pro Gly His Ile His Ile Thr Ser Thr Val Leu Asn Ile
    290                 295                 300

Phe Ala Val Leu Thr Ala Phe Phe Gly Ile Tyr Leu Gly Phe His Glu
```

```
                305                 310                 315                 320
Ala Ile Lys Gly Ile Ile Leu Asn Leu Leu Ser Arg Ile Ile Asp Thr
                    325                 330                 335

Lys Lys Ile Asn Ser Arg Val Leu Thr Leu Ala Ile Cys Ala Phe Ile
                340                 345                 350

Val Ile Thr Leu Thr Ile Trp Val Ser Phe Arg Val Ser Val Leu Val
            355                 360                 365

Phe Phe Gln Leu Gly Ser Pro Leu Tyr Gly Ile Val Ser Cys Leu Ile
        370                 375                 380

Pro Phe Phe Leu Ile Tyr Lys Val Ala Gln Leu Glu Lys Leu Arg Gly
385                 390                 395                 400

Phe Lys Ala Trp Leu Ile Leu Leu Tyr Gly Ile Leu Leu Cys Leu Ser
                405                 410                 415

Pro Leu Leu Lys Leu Ile Glu
            420

<210> SEQ ID NO 3
<211> LENGTH: 1335
<212> TYPE: DNA
<213> ORGANISM: Escherichia coli

<400> SEQUENCE: 3
atgattctgg acaccgttga cgaaaaaaag aaaggcgtgc atacccgcta tttaatatta      60
ctgattattt ttattgttac cgccgttaac tacgccgatc gtgcaacgct gtctattgct     120
ggtaccgaag tggcaaaaga gttgcagtta agtgcggttt cgatgggtta catcttctcc     180
gcttttggct gggcctactt gctgatgcaa atccccggcg gctggctgct tgataagttt     240
ggctcgaaaa aagtttacac ctacagcctc tttttctggt cgctattcac cttcctgcaa     300
ggctttgttg atatgttccc gctggcctgg cagggatct ccatgttctt tatgcgcttt      360
atgctcggct ctctcggaagc gccatcattc ccggcgaacg cccgaattgt cgccgcctgg     420
ttcccgacga agaacgtgg tactgcctcc gccatcttta actcggcgca atatttctcg      480
ctggcgctct tttcgccgct gcttggctgg ctgactttcg cctggggctg ggagcacgtc     540
tttaccgtta tggggtgat tggttttgtg ctgacggcgc tgtggatcaa gttgattcat      600
aacccgacag atcacccacg tatgtctgcg gaagagctga agtttatctc tgaaaatggc     660
gcggtggtcg atatggacca caaaaagccg ggcagtgcgg cagcaagcgg acccaaactg     720
cattacatca agcaattgct ctctaaccgc atgatgctgg cgtatttttt cggacaatat     780
tttatcaaca ccatcaccctg gttcttcctc acctggttcc cgatttatct ggtgcaggaa     840
aaaggcatgt cgattctgaa agtgggtctg gtcgcctcga ttccagcact gtgtggtttt     900
gcgggcggcg tgctgggagg tgtcttctcg gattatctga tcaaacgcgg tttatccctg     960
accctggcac gtaagctacc gattgtgctg ggaatgttgc tggcttccac catcatctta    1020
tgtaactaca ccaacaacac cacgctggtg gtcatgctga tggcgctggc tttctttggc    1080
aaaggatttg gtgcgctggg ctggccggtg atttctgaca ccgcgccgaa agagattgtt    1140
ggcctctgcg gcggcgtctt taacgtcttt ggcaatgttg cctccattgt cactccactg    1200
gtgattggct acctggtaag tgaactgcac tccttcaatg cagcactggt tttcgtggga    1260
tgttcagcgc tgatggcgat ggtctgctac ctcttcgtag ttggcgacat taaacgtatg    1320
gaattgcaga aataa                                                     1335

<210> SEQ ID NO 4
```

```
<211> LENGTH: 444
<212> TYPE: PRT
<213> ORGANISM: Escherichia coli

<400> SEQUENCE: 4
```

| | | | | | | | | | | | | | | |
|---|---|---|---|---|---|---|---|---|---|---|---|---|---|---|
| Met | Ile | Leu | Asp | Thr | Val | Asp | Glu | Lys | Lys | Gly | Val | His | Thr | Arg |
| 1 | | | | 5 | | | | | 10 | | | | | 15 |
| Tyr | Leu | Ile | Leu | Leu | Ile | Ile | Phe | Ile | Val | Thr | Ala | Val | Asn | Tyr | Ala |
| | | | | 20 | | | | | 25 | | | | | 30 | |
| Asp | Arg | Ala | Thr | Leu | Ser | Ile | Ala | Gly | Thr | Glu | Val | Ala | Lys | Glu | Leu |
| | | | 35 | | | | | 40 | | | | | 45 | | |
| Gln | Leu | Ser | Ala | Val | Ser | Met | Gly | Tyr | Ile | Phe | Ser | Ala | Phe | Gly | Trp |
| 50 | | | | | 55 | | | | | 60 | | | | | |
| Ala | Tyr | Leu | Leu | Met | Gln | Ile | Pro | Gly | Gly | Trp | Leu | Leu | Asp | Lys | Phe |
| 65 | | | | | 70 | | | | | 75 | | | | | 80 |
| Gly | Ser | Lys | Lys | Val | Tyr | Thr | Tyr | Ser | Leu | Phe | Phe | Trp | Ser | Leu | Phe |
| | | | | 85 | | | | | 90 | | | | | 95 | |
| Thr | Phe | Leu | Gln | Gly | Phe | Val | Asp | Met | Phe | Pro | Leu | Ala | Trp | Ala | Gly |
| | | | 100 | | | | | 105 | | | | | 110 | | |
| Ile | Ser | Met | Phe | Phe | Met | Arg | Phe | Met | Leu | Gly | Phe | Ser | Glu | Ala | Pro |
| | | 115 | | | | | 120 | | | | | 125 | | | |
| Ser | Phe | Pro | Ala | Asn | Ala | Arg | Ile | Val | Ala | Ala | Trp | Phe | Pro | Thr | Lys |
| 130 | | | | | 135 | | | | | 140 | | | | | |
| Glu | Arg | Gly | Thr | Ala | Ser | Ala | Ile | Phe | Asn | Ser | Ala | Gln | Tyr | Phe | Ser |
| 145 | | | | | 150 | | | | | 155 | | | | | 160 |
| Leu | Ala | Leu | Phe | Ser | Pro | Leu | Leu | Gly | Trp | Leu | Thr | Phe | Ala | Trp | Gly |
| | | | | 165 | | | | | 170 | | | | | 175 | |
| Trp | Glu | His | Val | Phe | Thr | Val | Met | Gly | Val | Ile | Gly | Phe | Val | Leu | Thr |
| | | | 180 | | | | | 185 | | | | | 190 | | |
| Ala | Leu | Trp | Ile | Lys | Leu | Ile | His | Asn | Pro | Thr | Asp | His | Pro | Arg | Met |
| | | 195 | | | | | 200 | | | | | 205 | | | |
| Ser | Ala | Glu | Glu | Leu | Lys | Phe | Ile | Ser | Glu | Asn | Gly | Ala | Val | Val | Asp |
| 210 | | | | | 215 | | | | | 220 | | | | | |
| Met | Asp | His | Lys | Lys | Pro | Gly | Ser | Ala | Ala | Ser | Gly | Pro | Lys | Leu |
| 225 | | | | | 230 | | | | | 235 | | | | | 240 |
| His | Tyr | Ile | Lys | Gln | Leu | Leu | Ser | Asn | Arg | Met | Met | Leu | Gly | Val | Phe |
| | | | | 245 | | | | | 250 | | | | | 255 | |
| Phe | Gly | Gln | Tyr | Phe | Ile | Asn | Thr | Ile | Thr | Trp | Phe | Phe | Leu | Thr | Trp |
| | | | 260 | | | | | 265 | | | | | 270 | | |
| Phe | Pro | Ile | Tyr | Leu | Val | Gln | Glu | Lys | Gly | Met | Ser | Ile | Leu | Lys | Val |
| | | 275 | | | | | 280 | | | | | 285 | | | |
| Gly | Leu | Val | Ala | Ser | Ile | Pro | Ala | Leu | Cys | Gly | Phe | Ala | Gly | Val |
| | 290 | | | | | 295 | | | | | 300 | | | | |
| Leu | Gly | Gly | Val | Phe | Ser | Asp | Tyr | Leu | Ile | Lys | Arg | Gly | Leu | Ser | Leu |
| 305 | | | | | 310 | | | | | 315 | | | | | 320 |
| Thr | Leu | Ala | Arg | Lys | Leu | Pro | Ile | Val | Leu | Gly | Met | Leu | Leu | Ala | Ser |
| | | | | 325 | | | | | 330 | | | | | 335 | |
| Thr | Ile | Ile | Leu | Cys | Asn | Tyr | Thr | Asn | Asn | Thr | Thr | Leu | Val | Val | Met |
| | | | | 340 | | | | | 345 | | | | | 350 | |
| Leu | Met | Ala | Leu | Ala | Phe | Phe | Gly | Lys | Gly | Phe | Gly | Ala | Leu | Gly | Trp |
| | | | | 355 | | | | | 360 | | | | | 365 | |
| Pro | Val | Ile | Ser | Asp | Thr | Ala | Pro | Lys | Glu | Ile | Val | Gly | Leu | Cys | Gly |
| | | 370 | | | | | 375 | | | | | 380 | | | |
| Gly | Val | Phe | Asn | Val | Phe | Gly | Asn | Val | Ala | Ser | Ile | Val | Thr | Pro | Leu |

```
                385                 390                 395                 400
Val Ile Gly Tyr Leu Val Ser Glu Leu His Ser Phe Asn Ala Ala Leu
                405                 410                 415

Val Phe Val Gly Cys Ser Ala Leu Met Ala Met Val Cys Tyr Leu Phe
                420                 425                 430

Val Val Gly Asp Ile Lys Arg Met Glu Leu Gln Lys
                435                 440
```

<210> SEQ ID NO 5
<211> LENGTH: 636
<212> TYPE: DNA
<213> ORGANISM: Escherichia coli

<400> SEQUENCE: 5

```
gtgttttctt attactttca aggtcttgca cttggggcgg ctatgatcct accgctcggt      60
ccacaaaatg ctttttgtgat gaatcagggc atacgtcgtc agtaccacat tatgattgcc    120
ttactttgtg ctatcagcga tttggtcctg atttgcgccg ggattttttgg tggcagcgcg    180
ttattgatgc agtcgccgtg gttgctggcg ctggtcacct ggggcggcgt agccttcttg    240
ctgtggtatg gttttggcgc tttttaaaaca gcaatgagca gtaatattga gttagccagc    300
gccgaagtca tgaagcaagg cagatggaaa attatcgcca ccatgttggc agtgacctgg    360
ctgaatccgc atgtttacct ggatactttt gttgtactgg gcagccttgg cgggcaactt    420
gatgtggaac caaaacgctg gtttgcactc gggacaatta gcgcctcttt cctgtggttc    480
tttggtctgg ctcttctcgc agcctggctg gcaccgcgtc tgcgcacggc aaaagcacag    540
cgcattatca atctggttgt gggatgtgtt atgtggttta ttgccttgca gctggcgaga    600
gacggtattg ctcatgcaca agccttgttc agttag                               636
```

<210> SEQ ID NO 6
<211> LENGTH: 211
<212> TYPE: PRT
<213> ORGANISM: Escherichia coli

<400> SEQUENCE: 6

```
Met Phe Ser Tyr Tyr Phe Gln Gly Leu Ala Leu Gly Ala Ala Met Ile
1               5                   10                  15

Leu Pro Leu Gly Pro Gln Asn Ala Phe Val Met Asn Gln Gly Ile Arg
                20                  25                  30

Arg Gln Tyr His Ile Met Ile Ala Leu Leu Cys Ala Ile Ser Asp Leu
            35                  40                  45

Val Leu Ile Cys Ala Gly Ile Phe Gly Gly Ser Ala Leu Leu Met Gln
        50                  55                  60

Ser Pro Trp Leu Leu Ala Leu Val Thr Trp Gly Gly Val Ala Phe Leu
65                  70                  75                  80

Leu Trp Tyr Gly Phe Gly Ala Phe Lys Thr Ala Met Ser Ser Asn Ile
                85                  90                  95

Glu Leu Ala Ser Ala Glu Val Met Lys Gln Gly Arg Trp Lys Ile Ile
                100                 105                 110

Ala Thr Met Leu Ala Val Thr Trp Leu Asn Pro His Val Tyr Leu Asp
            115                 120                 125

Thr Phe Val Val Leu Gly Ser Leu Gly Gly Gln Leu Asp Val Glu Pro
        130                 135                 140

Lys Arg Trp Phe Ala Leu Gly Thr Ile Ser Ala Ser Phe Leu Trp Phe
145                 150                 155                 160
```

Phe Gly Leu Ala Leu Leu Ala Ala Trp Leu Ala Pro Arg Leu Arg Thr
            165                 170                 175

Ala Lys Ala Gln Arg Ile Ile Asn Leu Val Val Gly Cys Val Met Trp
        180                 185                 190

Phe Ile Ala Leu Gln Leu Ala Arg Asp Gly Ile Ala His Ala Gln Ala
    195                 200                 205

Leu Phe Ser
    210

<210> SEQ ID NO 7
<211> LENGTH: 1470
<212> TYPE: DNA
<213> ORGANISM: Escherichia coli

<400> SEQUENCE: 7

| | |
|---|---|
| atggtttccg aaactaaaac cacagaagcg ccgggcttac gccgtgaatt aaaggcgcgt | 60 |
| cacctgacga tgattgccat tggcggttcc atcggtacag gtcttttttgt tgcctctggc | 120 |
| gcaacgattt ctcaggcagg tccgggcggg gcattgctct cgtatatgct gattggcctg | 180 |
| atggtttact tcctgatgac cagtctcggt gaactggctg catatatgcc ggtttccggt | 240 |
| tcgtttgcca cttacggtca gaactatgtt gaagaaggct ttggcttcgc gctgggctgg | 300 |
| aactactggt acaactgggc ggtgactatc gccgttgacc tggttgcagc tcagctggtc | 360 |
| atgagctggt ggttcccgga tacaccgggc tggatctgga gtgcgttgtt cctcggcgtt | 420 |
| atcttcctgc tgaactacat ctcagttcgt ggctttggtg aagcggaata ctggttctca | 480 |
| ctgatcaaag tcacgacagt tattgtcttt atcatcgttg gcgtgctgat gattatcggt | 540 |
| atcttcaaag gcgcgcagcc tgcgggctgg agcaactgga caatcggcga agcgccgttt | 600 |
| gctggtggtt ttgcgcgcga tatcggcgta gctatgattg tcggcttctc tttccaggga | 660 |
| accgagctga tcggtattgc tgcaggcgag tccgaagatc cggcgaaaaa cattccacgc | 720 |
| gcggtacgtc aggtgttctg gcgaatcctg ttgttctatg tgttcgcgat cctgattatc | 780 |
| agcctgatta ttccgtacac cgatccgagc ctgctgcgta cgatgttaa agacatcagc | 840 |
| gttagtccgt tcaccctggt gttccagcac gcgggtctgc tctctgcggc ggcggtgatg | 900 |
| aacgcagtta ttctgacggc ggtgctgtca gcgggtaact ccggtatgta tgcgtctact | 960 |
| cgtatgctgt acaccctggc gtgtgacggt aaagcgccgc gcattttcgc taaactgtcg | 1020 |
| cgtggtggcg tgccgcgtaa tgcgctgtat gcgacgacgg tgattgccgg tctgtgcttc | 1080 |
| ctgacctcca tgtttggcaa ccagacggta tacctgtggc tgctgaacac ctccgggatg | 1140 |
| acgggtttta tcgcctggct ggggattgcc attagccact atcgcttccg tcgcggttac | 1200 |
| gtattgcagg acacgacat taacgatctg ccgtaccgtt caggtttctt cccactgggg | 1260 |
| ccgatcttcg cattcattct gtgtctgatt atcactttgg ccagaactac gaagcgttc | 1320 |
| ctgaaagata ctattgactg ggcggcgta gcggcaacgt atattggtat cccgctgttc | 1380 |
| ctgattattt ggttcggcta caagctgatt aaaggaactc acttcgtacg ctacagcgaa | 1440 |
| atgaagttcc cgcagaacga taagaaataa | 1470 |

<210> SEQ ID NO 8
<211> LENGTH: 489
<212> TYPE: PRT
<213> ORGANISM: Escherichia coli

<400> SEQUENCE: 8

Met Val Ser Glu Thr Lys Thr Thr Glu Ala Pro Gly Leu Arg Arg Glu

```
            1               5                   10                  15
        Leu Lys Ala Arg His Leu Thr Met Ile Ala Ile Gly Gly Ser Ile Gly
                        20                  25                  30

Thr Gly Leu Phe Val Ala Ser Gly Ala Thr Ile Ser Gln Ala Gly Pro
                        35                  40                  45

Gly Gly Ala Leu Leu Ser Tyr Met Leu Ile Gly Leu Met Val Tyr Phe
                        50                  55                  60

Leu Met Thr Ser Leu Gly Glu Leu Ala Ala Tyr Met Pro Val Ser Gly
        65                  70                  75                  80

Ser Phe Ala Thr Tyr Gly Gln Asn Tyr Val Glu Glu Gly Phe Gly Phe
                        85                  90                  95

Ala Leu Gly Trp Asn Tyr Trp Tyr Asn Trp Ala Val Thr Ile Ala Val
                        100                 105                 110

Asp Leu Val Ala Ala Gln Leu Val Met Ser Trp Trp Phe Pro Asp Thr
                        115                 120                 125

Pro Gly Trp Ile Trp Ser Ala Leu Phe Leu Gly Val Ile Phe Leu Leu
                        130                 135                 140

Asn Tyr Ile Ser Val Arg Gly Phe Gly Glu Ala Glu Tyr Trp Phe Ser
        145                 150                 155                 160

Leu Ile Lys Val Thr Thr Val Ile Val Phe Ile Ile Val Gly Val Leu
                        165                 170                 175

Met Ile Ile Gly Ile Phe Lys Gly Ala Gln Pro Ala Gly Trp Ser Asn
                        180                 185                 190

Trp Thr Ile Gly Glu Ala Pro Phe Ala Gly Gly Phe Ala Ala Met Ile
                        195                 200                 205

Gly Val Ala Met Ile Val Gly Phe Ser Phe Gln Gly Thr Glu Leu Ile
                        210                 215                 220

Gly Ile Ala Ala Gly Glu Ser Glu Asp Pro Ala Lys Asn Ile Pro Arg
        225                 230                 235                 240

Ala Val Arg Gln Val Phe Trp Arg Ile Leu Leu Phe Tyr Val Phe Ala
                        245                 250                 255

Ile Leu Ile Ile Ser Leu Ile Ile Pro Tyr Thr Asp Pro Ser Leu Leu
                        260                 265                 270

Arg Asn Asp Val Lys Asp Ile Ser Val Ser Pro Phe Thr Leu Val Phe
                        275                 280                 285

Gln His Ala Gly Leu Leu Ser Ala Ala Val Met Asn Ala Val Ile
                        290                 295                 300

Leu Thr Ala Val Leu Ser Ala Gly Asn Ser Gly Met Tyr Ala Ser Thr
        305                 310                 315                 320

Arg Met Leu Tyr Thr Leu Ala Cys Asp Gly Lys Ala Pro Arg Ile Phe
                        325                 330                 335

Ala Lys Leu Ser Arg Gly Gly Val Pro Arg Asn Ala Leu Tyr Ala Thr
                        340                 345                 350

Thr Val Ile Ala Gly Leu Cys Phe Leu Thr Ser Met Phe Gly Asn Gln
                        355                 360                 365

Thr Val Tyr Leu Trp Leu Leu Asn Thr Ser Gly Met Thr Gly Phe Ile
                        370                 375                 380

Ala Trp Leu Gly Ile Ala Ile Ser His Tyr Arg Phe Arg Arg Gly Tyr
        385                 390                 395                 400

Val Leu Gln Gly His Asp Ile Asn Asp Leu Pro Tyr Arg Ser Gly Phe
                        405                 410                 415

Phe Pro Leu Gly Pro Ile Phe Ala Phe Ile Leu Cys Leu Ile Ile Thr
                        420                 425                 430
```

Leu Gly Gln Asn Tyr Glu Ala Phe Leu Lys Asp Thr Ile Asp Trp Gly
         435                 440                 445

Gly Val Ala Ala Thr Tyr Ile Gly Ile Pro Leu Phe Leu Ile Ile Trp
    450                 455                 460

Phe Gly Tyr Lys Leu Ile Lys Gly Thr His Phe Val Arg Tyr Ser Glu
465                 470                 475                 480

Met Lys Phe Pro Gln Asn Asp Lys Lys
             485

<210> SEQ ID NO 9
<211> LENGTH: 1194
<212> TYPE: DNA
<213> ORGANISM: Escherichia coli

<400> SEQUENCE: 9

```
atgaacaaaa acagagggtt tacgcctctg gcggtcgttc tgatgctctc aggcagctta      60
gccctaacag atgtgacga caaacaggcc caacaaggtg ccagcagat gcccgccgtt      120
ggcgtagtaa cagtcaaaac tgaacctctg cagatcacaa ccgagcttcc gggtcgcacc      180
agtgcctacc ggatcgcaga agttcgtcct caagttagcg ggattatcct gaagcgtaat      240
ttcaaagaag gtagcgacat cgaagcaggt gtctctctct atcagattga tcctgcgacc      300
tatcaggcga catacgacag tgcgaaaggt gatctggcga agcccaggc tgcagccaat      360
atcgcgcaat tgacggtgaa tcgttatcag aaactgctcg gtactcagta catcagtaag      420
caagagtacg atcaggctct ggctgatgcg caacaggcga atgctgcggt aactgcggcg      480
aaagctgccg ttgaaactgc gcggatcaat ctggcttaca ccaaagtcac ctctccgatt      540
agcggtcgca ttggtaagtc gaacgtgacg gaaggcgcat ggtacagaa cggtcaggcg      600
actgcgctgg caaccgtgca gcaacttgat ccgatctacg ttgatgtgac ccagtccagc      660
aacgacttcc tgcgcctgaa acaggaactg gcgaatggca cgctgaaaca agagaacggc      720
aaagccaaag tgtcactgat caccagtgac ggcattaagt tcccgcagga cggtacgctg      780
gaattctctg acgttaccgt tgatcagacc actgggtcta tcaccctacg cgctatcttc      840
ccgaacccgg atcacactct gctgccgggt atgttcgtgc gcgcacgtct ggaagaaggg      900
cttaatccaa cgctatttt agtcccgcaa cagggcgtaa cccgtacgcc gcgtggcgat      960
gccaccgtac tggtagttgg cgcggatgac aaagtggaaa cccgtccgat cgttgcaagc     1020
caggctattg cgataagtg gctggtgaca gaaggtctga agcaggcga tcgcgtagta     1080
ataagtgggc tgcagaaagt gcgtcctggt gtccaggtaa aagcacaaga agttaccgct     1140
gataataacc agcaagccgc aagcggtgct cagcctgaac agtccaagtc ttaa          1194
```

<210> SEQ ID NO 10
<211> LENGTH: 397
<212> TYPE: PRT
<213> ORGANISM: Escherichia coli

<400> SEQUENCE: 10

Met Asn Lys Asn Arg Gly Phe Thr Pro Leu Ala Val Val Leu Met Leu
1               5                   10                  15

Ser Gly Ser Leu Ala Leu Thr Gly Cys Asp Asp Lys Gln Ala Gln Gln
                20                  25                  30

Gly Gly Gln Gln Met Pro Ala Val Gly Val Val Thr Val Lys Thr Glu
         35                  40                  45

Pro Leu Gln Ile Thr Thr Glu Leu Pro Gly Arg Thr Ser Ala Tyr Arg

```
                50                  55                  60
Ile Ala Glu Val Arg Pro Gln Val Ser Gly Ile Ile Leu Lys Arg Asn
 65                  70                  75                  80

Phe Lys Glu Gly Ser Asp Ile Glu Ala Gly Val Ser Leu Tyr Gln Ile
                 85                  90                  95

Asp Pro Ala Thr Tyr Gln Ala Thr Tyr Asp Ser Ala Lys Gly Asp Leu
                100                 105                 110

Ala Lys Ala Gln Ala Ala Asn Ile Ala Gln Leu Thr Val Asn Arg
                115                 120                 125

Tyr Gln Lys Leu Leu Gly Thr Gln Tyr Ile Ser Lys Gln Glu Tyr Asp
                130                 135                 140

Gln Ala Leu Ala Asp Ala Gln Ala Asn Ala Ala Val Thr Ala Ala
145                 150                 155                 160

Lys Ala Ala Val Glu Thr Ala Arg Ile Asn Leu Ala Tyr Thr Lys Val
                165                 170                 175

Thr Ser Pro Ile Ser Gly Arg Ile Gly Lys Ser Asn Val Thr Glu Gly
                180                 185                 190

Ala Leu Val Gln Asn Gly Gln Ala Thr Ala Leu Ala Thr Val Gln Gln
                195                 200                 205

Leu Asp Pro Ile Tyr Val Asp Val Thr Gln Ser Ser Asn Asp Phe Leu
                210                 215                 220

Arg Leu Lys Gln Glu Leu Ala Asn Gly Thr Leu Lys Gln Glu Asn Gly
225                 230                 235                 240

Lys Ala Lys Val Ser Leu Ile Thr Ser Asp Gly Ile Lys Phe Pro Gln
                245                 250                 255

Asp Gly Thr Leu Glu Phe Ser Asp Val Thr Val Asp Gln Thr Thr Gly
                260                 265                 270

Ser Ile Thr Leu Arg Ala Ile Phe Pro Asn Pro Asp His Thr Leu Leu
                275                 280                 285

Pro Gly Met Phe Val Arg Ala Arg Leu Glu Glu Gly Leu Asn Pro Asn
                290                 295                 300

Ala Ile Leu Val Pro Gln Gln Gly Val Thr Arg Thr Pro Arg Gly Asp
305                 310                 315                 320

Ala Thr Val Leu Val Val Gly Ala Asp Asp Lys Val Glu Thr Arg Pro
                325                 330                 335

Ile Val Ala Ser Gln Ala Ile Gly Asp Lys Trp Leu Val Thr Glu Gly
                340                 345                 350

Leu Lys Ala Gly Asp Arg Val Val Ile Ser Gly Leu Gln Lys Val Arg
                355                 360                 365

Pro Gly Val Gln Val Lys Ala Gln Glu Val Thr Ala Asp Asn Asn Gln
                370                 375                 380

Gln Ala Ala Ser Gly Ala Gln Pro Glu Gln Ser Lys Ser
385                 390                 395

<210> SEQ ID NO 11
<211> LENGTH: 3150
<212> TYPE: DNA
<213> ORGANISM: Escherichia coli

<400> SEQUENCE: 11
atgcctaatt tctttatcga tcgcccgatt tttgcgtggg tgatcgccat tatcatcatg      60
ttggcagggg ggctggcgat cctcaaactg ccggtggcgc aatatcctac gattgcaccg     120
ccggcagtaa cgatctccgc ctcctacccc ggcgctgatg cgaaaacagt gcaggacacg     180
```

-continued

```
gtgacacagg ttatcgaaca gaatatgaac ggtatcgata acctgatgta catgtcctct    240
aacagtgact ccacgggtac cgtgcagatc accctgacct ttgagtctgg tactgatgcg    300
gatatcgcgc aggttcaggt gcagaacaaa ctgcagctgg cgatgccgtt gctgccgcaa    360
gaagttcagc agcaagggt gagcgttgag aaatcatcca gcagcttcct gatggttgtc    420
ggcgttatca acaccgatgg caccatgacg caggaggata tctccgacta cgtggcggcg    480
aatatgaaag atgccatcag ccgtacgtcg ggcgtgggtg atgttcagtt gttcggttca    540
cagtacgcga tgcgtatctg gatgaacccg aatgagctga acaaattcca gctaacgccg    600
gttgatgtca ttaccgccat caaagcgcag aacgcccagg ttgcggcggg tcagctcggt    660
ggtacgccgc cggtgaaagg ccaacagctt aacgcctcta ttattgctca gacgcgtctg    720
acctctactg aagagttcgg caaaatcctg ctgaaagtga atcaggatgg ttcccgcgtg    780
ctgctgcgtg acgtcgcgaa gattgagctg ggtggtgaga actacgacat catcgcagag    840
tttaacggcc aaccggcttc cggtctgggg atcaagctgg cgaccggtgc aaacgcgctg    900
gataccgctg cggcaatccg tgctgaactg gcgaagatga accgttctt cccgtcgggt    960 ctgaaaattg tttacccata cgacaccacg ccgttcgtga aaatctctat tcacgaagtg   1020
gttaaaacgc tggtcgaagc gatcatcctc gtgttcctgg ttatgtatct gttcctgcag   1080
aacttccgcg cgacgttgat tccgaccatt gccgtaccgg tggtattgct cgggacctt    1140 gccgtccttg ccgcctttgg cttctcgata aacacgctaa caatgttcgg gatggtgctc   1200
gccatcggcc tgttggtgga tgacgccatc gttgtggtag aaaacgttga gcgtgttatg   1260
gcggaagaag gtttgccgcc aaaagaagct acccgtaagt cgatggggca gattcagggc   1320
gctctggtcg gtatcgcgat ggtactgtcg gcggtattcg taccgatggc cttcttggc    1380 ggttctactg tgtgctatcta tcgtcagttc tctattacca ttgtttcagc aatggcgctg   1440
tcggtactgg tggcgttgat cctgactcca gctctttgtg ccaccatgct gaaaccgatt   1500
gccaaaggcg atcacgggga aggtaaaaaa ggcttcttcg gctggtttaa ccgcatgttc   1560
gagaagagca cgcaccacta caccgacagc gtaggcggta ttctgcgcag tacggggcgt   1620
tacctggtgc tgtatctgat catcgtggtc ggcatggcct atctgttcgt gcgtctgcca   1680
agctccttct tgccagatga ggaccagggc gtgtttatga ccatggttca gctgccagca   1740
ggtgcaacgc aggaacgtac acagaaagtg ctcaatgagg taacgcatta ctatctgacc   1800
aaagaaaaga caacgttga gtcggtgttc gccgttaacg gcttcggctt tgcgggacgt   1860
ggtcagaata ccggtattgc gttcgtttcc ttgaaggact gggccgatcg tccgggcgaa   1920
gaaaacaaag ttgaagcgat taccatgcgt gcaacacgcg ctttctcgca aatcaaagat   1980
gcgatggttt tcgcctttaa cctgcccgca atcgtggaac tgggtactgc aaccggcttt   2040
gactttgagc tgattgacca ggctggcctt ggtcacgaaa aactgactca ggcgcgtaac   2100
cagttgcttg cagaagcagc gaagcaccct gatatgttga ccagcgtacg tccaaacggt   2160
ctggaagata ccccgcagtt taagattgat atcgaccagg aaaaagcgca ggcgctgggt   2220
gtttctatca acgacattaa caccactctg ggcgctgcat ggggcggcag ctatgtgaac   2280
gactttatcg accgcggtcg tgtgaagaaa gtttatgtca tgtcagaagc gaaataccgt   2340
atgctgccgg atgatatcgg cgactggtat gttcgtgctg ctgatggtca gatggtgcca   2400
ttctcggcgt tctcctcttc tcgttgggag tacggttcgc cgcgtctgga acgttacaac   2460
ggcctgccat ccatggaaat cttaggccag gcggcaccgg taaaagtac cggtgaagca   2520 atggagctga tggaacaact ggcgagcaaa ctgcctaccg gtgttggcta tgactggacg   2580
```

```
gggatgtcct atcaggaacg tctctccggc aaccaggcac cttcactgta cgcgatttcg   2640
ttgattgtcg tgttcctgtg tctggcggcg ctgtacgaga gctggtcgat ccgttctcc    2700 gttatgctgg tcgttccgct gggggttatc ggtgcgttgc tggctgccac cttccgtggc   2760
ctgaccaatg acgtttactt ccaggtaggc ctgctcacaa ccattgggtt gtcggcgaag   2820
aacgcgatcc ttatcgtcga attcgccaaa gacttgatgg ataaagaagg taaaggtctg   2880
attgaagcga cgcttgatgc ggtgcggatg cgtttacgtc cgatcctgat gacctcgctg   2940
gcgtttatcc tcggcgttat gccgctggtt atcagtactg gtgctggttc cggcgcgcag   3000
aacgcagtag gtaccggtgt aatgggcggg atggtgaccg caacggtact ggcaatcttc   3060
ttcgttccgg tattctttgt ggtggttcgc cgccgcttta gccgcaagaa tgaagatatc   3120
gagcacagcc atactgtcga tcatcattga                                    3150
```

<210> SEQ ID NO 12
<211> LENGTH: 1049
<212> TYPE: PRT
<213> ORGANISM: Escherichia coli

<400> SEQUENCE: 12

```
Met Pro Asn Phe Phe Ile Asp Arg Pro Ile Phe Ala Trp Val Ile Ala
1               5                   10                  15

Ile Ile Ile Met Leu Ala Gly Gly Leu Ala Ile Leu Lys Leu Pro Val
            20                  25                  30

Ala Gln Tyr Pro Thr Ile Ala Pro Pro Ala Val Thr Ile Ser Ala Ser
        35                  40                  45

Tyr Pro Gly Ala Asp Ala Lys Thr Val Gln Asp Thr Val Thr Gln Val
    50                  55                  60

Ile Glu Gln Asn Met Asn Gly Ile Asp Asn Leu Met Tyr Met Ser Ser
65                  70                  75                  80

Asn Ser Asp Ser Thr Gly Thr Val Gln Ile Thr Leu Thr Phe Glu Ser
                85                  90                  95

Gly Thr Asp Ala Asp Ile Ala Gln Val Gln Val Gln Asn Lys Leu Gln
            100                 105                 110

Leu Ala Met Pro Leu Leu Pro Gln Glu Val Gln Gln Gly Val Ser
        115                 120                 125

Val Glu Lys Ser Ser Ser Phe Leu Met Val Gly Val Ile Asn
    130                 135                 140

Thr Asp Gly Thr Met Thr Gln Glu Asp Ile Ser Asp Tyr Val Ala Ala
145                 150                 155                 160

Asn Met Lys Asp Ala Ile Ser Arg Thr Ser Gly Val Gly Asp Val Gln
                165                 170                 175

Leu Phe Gly Ser Gln Tyr Ala Met Arg Ile Trp Met Asn Pro Asn Glu
            180                 185                 190

Leu Asn Lys Phe Gln Leu Thr Pro Val Asp Val Ile Thr Ala Ile Lys
        195                 200                 205

Ala Gln Asn Ala Gln Val Ala Ala Gly Gln Leu Gly Gly Thr Pro Pro
    210                 215                 220

Val Lys Gly Gln Gln Leu Asn Ala Ser Ile Ile Ala Gln Thr Arg Leu
225                 230                 235                 240

Thr Ser Thr Glu Glu Phe Gly Lys Ile Leu Leu Lys Val Asn Gln Asp
                245                 250                 255

Gly Ser Arg Val Leu Leu Arg Asp Val Ala Lys Ile Glu Leu Gly Gly
            260                 265                 270
```

-continued

Glu Asn Tyr Asp Ile Ile Ala Glu Phe Asn Gly Gln Pro Ala Ser Gly
            275                 280                 285

Leu Gly Ile Lys Leu Ala Thr Gly Ala Asn Ala Leu Asp Thr Ala Ala
    290                 295                 300

Ala Ile Arg Ala Glu Leu Ala Lys Met Glu Pro Phe Phe Pro Ser Gly
305                 310                 315                 320

Leu Lys Ile Val Tyr Pro Tyr Asp Thr Thr Pro Phe Val Lys Ile Ser
                325                 330                 335

Ile His Glu Val Val Lys Thr Leu Val Glu Ala Ile Ile Leu Val Phe
                340                 345                 350

Leu Val Met Tyr Leu Phe Leu Gln Asn Phe Arg Ala Thr Leu Ile Pro
            355                 360                 365

Thr Ile Ala Val Pro Val Val Leu Leu Gly Thr Phe Ala Val Leu Ala
    370                 375                 380

Ala Phe Gly Phe Ser Ile Asn Thr Leu Thr Met Phe Gly Met Val Leu
385                 390                 395                 400

Ala Ile Gly Leu Leu Val Asp Asp Ala Ile Val Val Glu Asn Val
                405                 410                 415

Glu Arg Val Met Ala Glu Gly Leu Pro Pro Lys Glu Ala Thr Arg
            420                 425                 430

Lys Ser Met Gly Gln Ile Gln Gly Ala Leu Val Gly Ile Ala Met Val
    435                 440                 445

Leu Ser Ala Val Phe Val Pro Met Ala Phe Phe Gly Gly Ser Thr Gly
    450                 455                 460

Ala Ile Tyr Arg Gln Phe Ser Ile Thr Ile Val Ser Ala Met Ala Leu
465                 470                 475                 480

Ser Val Leu Val Ala Leu Ile Leu Thr Pro Ala Leu Cys Ala Thr Met
                485                 490                 495

Leu Lys Pro Ile Ala Lys Gly Asp His Gly Glu Gly Lys Lys Gly Phe
            500                 505                 510

Phe Gly Trp Phe Asn Arg Met Phe Glu Lys Ser Thr His His Tyr Thr
    515                 520                 525

Asp Ser Val Gly Gly Ile Leu Arg Ser Thr Gly Arg Tyr Leu Val Leu
    530                 535                 540

Tyr Leu Ile Ile Val Val Gly Met Ala Tyr Leu Phe Val Arg Leu Pro
545                 550                 555                 560

Ser Ser Phe Leu Pro Asp Glu Asp Gln Gly Val Phe Met Thr Met Val
                565                 570                 575

Gln Leu Pro Ala Gly Ala Thr Gln Glu Arg Thr Gln Lys Val Leu Asn
            580                 585                 590

Glu Val Thr His Tyr Tyr Leu Thr Lys Glu Lys Asn Asn Val Glu Ser
    595                 600                 605

Val Phe Ala Val Asn Gly Phe Gly Phe Ala Gly Arg Gly Gln Asn Thr
610                 615                 620

Gly Ile Ala Phe Val Ser Leu Lys Asp Trp Asp Arg Pro Gly Glu
625                 630                 635                 640

Glu Asn Lys Val Glu Ala Ile Thr Met Arg Ala Thr Arg Ala Phe Ser
                645                 650                 655

Gln Ile Lys Asp Ala Met Val Phe Ala Phe Asn Leu Pro Ala Ile Val
            660                 665                 670

Glu Leu Gly Thr Ala Thr Gly Phe Asp Phe Glu Leu Ile Asp Gln Ala
            675                 680                 685

```
Gly Leu Gly His Glu Lys Leu Thr Gln Ala Arg Asn Gln Leu Leu Ala
    690                 695                 700

Glu Ala Ala Lys His Pro Asp Met Leu Thr Ser Val Arg Pro Asn Gly
705                 710                 715                 720

Leu Glu Asp Thr Pro Gln Phe Lys Ile Asp Ile Asp Gln Glu Lys Ala
                725                 730                 735

Gln Ala Leu Gly Val Ser Ile Asn Asp Ile Asn Thr Thr Leu Gly Ala
            740                 745                 750

Ala Trp Gly Gly Ser Tyr Val Asn Asp Phe Ile Asp Arg Gly Arg Val
        755                 760                 765

Lys Lys Val Tyr Val Met Ser Glu Ala Lys Tyr Arg Met Leu Pro Asp
    770                 775                 780

Asp Ile Gly Asp Trp Tyr Val Arg Ala Ala Asp Gly Gln Met Val Pro
785                 790                 795                 800

Phe Ser Ala Phe Ser Ser Arg Trp Glu Tyr Gly Ser Pro Arg Leu
                805                 810                 815

Glu Arg Tyr Asn Gly Leu Pro Ser Met Glu Ile Leu Gly Gln Ala Ala
                820                 825                 830

Pro Gly Lys Ser Thr Gly Glu Ala Met Glu Leu Met Glu Gln Leu Ala
            835                 840                 845

Ser Lys Leu Pro Thr Gly Val Gly Tyr Asp Trp Thr Gly Met Ser Tyr
850                 855                 860

Gln Glu Arg Leu Ser Gly Asn Gln Ala Pro Ser Leu Tyr Ala Ile Ser
865                 870                 875                 880

Leu Ile Val Val Phe Leu Cys Leu Ala Ala Leu Tyr Glu Ser Trp Ser
                885                 890                 895

Ile Pro Phe Ser Val Met Leu Val Val Pro Leu Gly Val Ile Gly Ala
                900                 905                 910

Leu Leu Ala Ala Thr Phe Arg Gly Leu Thr Asn Asp Val Tyr Phe Gln
            915                 920                 925

Val Gly Leu Leu Thr Thr Ile Gly Leu Ser Ala Lys Asn Ala Ile Leu
    930                 935                 940

Ile Val Glu Phe Ala Lys Asp Leu Met Asp Lys Glu Gly Lys Gly Leu
945                 950                 955                 960

Ile Glu Ala Thr Leu Asp Ala Val Arg Met Arg Leu Arg Pro Ile Leu
                965                 970                 975

Met Thr Ser Leu Ala Phe Ile Leu Gly Val Met Pro Leu Val Ile Ser
            980                 985                 990

Thr Gly Ala Gly Ser Gly Ala Gln Asn Ala Val Gly Thr Gly Val Met
        995                 1000                1005

Gly Gly Met Val Thr Ala Thr Val Leu Ala Ile Phe Phe Val Pro
    1010                1015                1020

Val Phe Phe Val Val Arg Arg Arg Phe Ser Arg Lys Asn Glu
    1025                1030                1035

Asp Ile Glu His Ser His Thr Val Asp His His
    1040                1045

<210> SEQ ID NO 13
<211> LENGTH: 30
<212> TYPE: DNA
<213> ORGANISM: Artificial
<220> FEATURE:
<223> OTHER INFORMATION: Promoter

<400> SEQUENCE: 13
```
aactgttaat tagtaggccg agcatattac                                    30

<210> SEQ ID NO 14
<211> LENGTH: 46
<212> TYPE: DNA
<213> ORGANISM: Artificial
<220> FEATURE:
<223> OTHER INFORMATION: Promoter

<400> SEQUENCE: 14
aaaaagagta ttgacttcgc atcttttgt acctataatg tgtgga                   46

<210> SEQ ID NO 15
<211> LENGTH: 35
<212> TYPE: DNA
<213> ORGANISM: Artificial
<220> FEATURE:
<223> OTHER INFORMATION: Promoter

<400> SEQUENCE: 15
tttacagcta gctcagtcct aggtattatg ctagc                              35

<210> SEQ ID NO 16
<211> LENGTH: 35
<212> TYPE: DNA
<213> ORGANISM: Artificial
<220> FEATURE:
<223> OTHER INFORMATION: Promoter

<400> SEQUENCE: 16
tttacggcta gctcagccct aggtattatg ctagc                              35

<210> SEQ ID NO 17
<211> LENGTH: 35
<212> TYPE: DNA
<213> ORGANISM: Artificial
<220> FEATURE:
<223> OTHER INFORMATION: Promoter

<400> SEQUENCE: 17
ttgacggcta gctcagtcct aggtacagtg ctagc                              35

<210> SEQ ID NO 18
<211> LENGTH: 29
<212> TYPE: DNA
<213> ORGANISM: Artificial
<220> FEATURE:
<223> OTHER INFORMATION: RBS sequence
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 18
tcttaatcat gcnnnggann nttaacttt                                     29

<210> SEQ ID NO 19
<211> LENGTH: 29
<212> TYPE: DNA
<213> ORGANISM: Artificial
<220> FEATURE:
<223> OTHER INFORMATION: 5'UTR

<400> SEQUENCE: 19

```
tcttaatcat gcggggagt gttaacttt                                         29

<210> SEQ ID NO 20
<211> LENGTH: 29
<212> TYPE: DNA
<213> ORGANISM: Artificial
<220> FEATURE:
<223> OTHER INFORMATION: 5'UTR sequence

<400> SEQUENCE: 20
tcttaatcat gcgttggagg attaacttt                                        29

<210> SEQ ID NO 21
<211> LENGTH: 29
<212> TYPE: DNA
<213> ORGANISM: Artificial
<220> FEATURE:
<223> OTHER INFORMATION: 5'UTR sequence

<400> SEQUENCE: 21
tcttaatcat gccggggacg gttaacttt                                        29

<210> SEQ ID NO 22
<211> LENGTH: 29
<212> TYPE: DNA
<213> ORGANISM: Artificial
<220> FEATURE:
<223> OTHER INFORMATION: 5'UTR sequence

<400> SEQUENCE: 22
tcttaatcat gctggggagg gttaacttt                                        29
```